United States Patent
Chen et al.

(10) Patent No.: US 9,994,919 B2
(45) Date of Patent: Jun. 12, 2018

(54) FLOURY 2 GENE-SPECIFIC ASSAY IN MAIZE FOR FLOURY (FL2) TRAIT INTROGRESSION

(71) Applicants: DOW AGROSCIENCES LLC, Indianapolis, IN (US); Wei Chen, Carmel, IN (US); Nathan Van Opdorp, Geneseo, IL (US); Steve Plehn, Juneau, WI (US); Nadia Chaidir, Carmel, IN (US)

(72) Inventors: Wei Chen, Carmel, IN (US); Nathan Van Opdorp, Geneseo, IL (US); Steve Plehn, Juneau, WI (US); Peter Friedemann, Philo, IL (US); Nadia Chaidir, Carmel, IN (US); Siva Prasad Kumpatla, Carmel, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days. days.

(21) Appl. No.: 14/403,648

(22) PCT Filed: May 29, 2013

(86) PCT No.: PCT/US2013/042997
§ 371 (c)(1),
(2) Date: Nov. 25, 2014

(87) PCT Pub. No.: WO2015/012783
PCT Pub. Date: Jan. 29, 2015

(65) Prior Publication Data
US 2016/0153055 A1 Jun. 2, 2016

Related U.S. Application Data

(60) Provisional application No. 61/653,287, filed on May 30, 2012.

(51) Int. Cl.
*C12Q 1/6895* (2018.01)
*C12Q 1/68* (2018.01)

(52) U.S. Cl.
CPC ........ *C12Q 1/6895* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2011/0283427 A1   11/2011   Wei et al.

FOREIGN PATENT DOCUMENTS

EP    1726664 A1    11/2006
WO    1998/02563    1/1998

OTHER PUBLICATIONS

Coleman et al 1995 PNAS 92:6828-6831.*
Xu et al 2012 PLoS ONE 7(1): e22900.doi:10.1371/journal.pone.0022900.*
Swift-Scanlan et al 2006 BioTechniques 40:210-219.*
Cortes et al 2011 Theor. Appl. Genet 123:827-845.*
Gillikin et al 1997 Plant Physiology 114:345-352.*
Coleman et al., 1995, A Defective Signal Peptide in the Maize High-Lysine Mutatnt Floury 2, PNAS, 92: 6828-6831.
Rosso et al., 2011, Devlopment of breeder-friendly markers for selection of MIPS1 mutation in soybean, Mol Breeding, 28: 127-132.
Song et al, 2003, Gene expression of a gene family in maize based on noncollinear haplotypes, PNAS, 100(15): 9055-9060.
Song et al, 2001, Sequence, regulation, and evolution of the maize 22-kD alpha zein gene family, Genome Research, 1817-1825.
1994, Zea mays 24-kD alpha-zein gene (floury2), complete cds, retrieved from EBI accession No. EM-STD: L3430 (Reference not available/provided by Citing Authority—EESR).
1998, Maize floury2 gene (fl2), XP002755131, retrieved from EBI accession No. GSN: AAV09028.
2010, KASP Genotyping QuickStart Guide, Retrieved from internet at URL:http://web.archive.org/web/20100602045208/http://www.kbioseience.co.uk/download/KASP manual.pdf.
1999, Zea mays cosmid IV.1E1 22-kDa alpha zein protein 21 (azs22-16) gene, complete cds; retrotransposon Opie-2 gag protein, polyprotein, and copia protein genes, retrieved from EBI accession No. EM_STD:AF090446 (Reference not available/provided by Citing Authority—EESR).
2003, Zea mays cultivar B73 chromosome 4S sequenced frament from BAC ZMMBBb282F18, which containing the 22 kDa gene copy of azs22.16 (floury2), complete sequence, retrieved from EBI accession No. EM_STD:AC144717 (Reference not available/provided by Citing Authority—EESR).
Extended European Search Report for European Application No. 13886630.6, dated Mar. 21, 2016.

* cited by examiner

*Primary Examiner* — Brent T Page
(74) *Attorney, Agent, or Firm* — Marcos P. Rivas; Barnes & Thornburg LLP

(57) ABSTRACT

The disclosure concerns compositions and methods for determining the zygosity of corn plants containing one or more floury2 (fl2) mutations. In embodiments, the disclosure concerns a gene specific PCR-based molecular (KASPar®) assay for identifying the floury2 trait in plants. In certain embodiments, compositions and methods are disclosed for determining the zygosity of corn plants with respect to the fl2 allele. In particular embodiments, the assay may be used for fl2 germplasm identification, accelerating introgression and molecular breeding programs in corn and other plants.

17 Claims, 18 Drawing Sheets

FIG. 1

```
B73   (SEQ ID NO:9)   GAGATCATGCATGTCATTCCACATAAATGAAAAGAATTCCTATATAAAAATGACATGTTT  60
NF7_3 (SEQ ID NO:13)  GAGATCATGCATGTCATTCCACATAAATGAAAAGAATTCCTATATAAAAATGACATGTTT  60
L34340(SEQ ID NO:10)  GAGATCATGCATGTCATTCCACATAAATGAATATGAATTCCTATATAAAAACGACATGTTT 60
FF2_1 (SEQ ID NO:11)  GAGATCATGCATGTCATTCCACATAAATGAAAAGAATTCCTATATAAAAACGACATGTTT  60
FF1_1 (SEQ ID NO:12)  GAGATCATGCATGTCATTCCACATAAATGAAAAGAATTCCTATATAAAAACGACATGTTT  60
                      *********************************   **********  *********

B73       TGTTGTAGGTAGTGGAAATTATCTTTCCAGCAAAGACCATATAATCCGATAAAGCTGATA  120
NF7_3     TGTTGTAGGTAGTGGAAATTATCTTTCCAGCAAAGACCATATAATCCGATAAAGCTGATA  120
L34340    TGTTGTAGGTAGTGGAAACTATCTTTCCAGCAAAGACCATATAATCCGATAAAGCTGATA  120
FF2_1     TGTTGTAGGTAGTGGAAACTATCTTTCCAGCAAAGACCATATAATCCGATAAAGCTGATA  120
FF1_1     TGTTGTAGGTAGTGGAAACTATCTTTCCAGCAAAGACCATAT AATCCGATAAAGCTGATA 120
                            ***  ********************** *****************

B73       ACTAAATGTCAAAATCGAGTAAGTGCCATATATCATCTATATC-TATCTGTGTTTGGAAAA  180
NF7_3     ACTAAATGTCAAAATCGAGTAAGTGCCATATATCATCTATATCTTATCTGTGTTTGGAAAA 180
L34340    ACTAAATGTCGAAATCGAGTAGGTGCCATATATCATCTATATCTTATCTGTGTTTGGAAAA 180
```

FIG. 1 (continued)

```
FF2_1    ACTAAATGTGAAATCGAGTAGGTGCCATATCATCTATATCTTATCTGTTGTTTGGAAAA  180
FF1_1    ACTAAATGTGAAATCGAGTAGGTGCCATATCATCTATATCTTATCTGTTGTTTGGAAAA  180
         ***********  ************************************************

B73      AGACAAAATCCAAAAAAAAATATATGAGATCTCACATGTATAAATAGCTCCCAAATCAGTA  240
NF7_3    AGACAAAATCCAAAAAAAAATATATGAGATCTCACATGTATAAATAGCTCCCAAATCAGTA  240
L34340   AGACAAAATCCAAAAAAAAATATATGAGATCTCACCTGTATAAATAGCTCCCAAATCAGTA  240
FF2_1    AGACAAAATCCAAAAAAAAATATATGAGATCTCACTTGTATAAATAGCTCCCAAATCAGTA  240
FF1_1    AGACAAAATCCAAAAAAAAATATATGAGATCTCACTTGTATAAATAGCTCCCAAATCAGTA  240
         ***********************************  ***********************

B73      GTTAATACATCTCCCATAATATTTCAGCATTCAAAAACACACCAAGCGAAGCGCACTAG   300
NF7_3    GTTAATACATCTCCCATAATATTTCAGCATTCAAAAACACACCAAGCGAAGCGCACTAG   300
L34340   GTTAATACATCTCCCATAATATTTCAGCATTCAGAAACACACCAAGCGAA-CG-ACTAG   298
FF2_1    GTTAATACATCTCCCATAATATTTCAGCATTCAGAAACACACCAAGCGAAGCGCACTAG   300
FF1_1    GTTAATACATCTCCCATAATATTTCAGCATTCAGAAACACACCAAGCGAAGCGCACTAG   300
         ********************************* ****************  ******
```

FIG. 1 (continued)

```
B73       CAACGACCTAACACCAATGGCTACCAAGATATTAGCCCTCCTTGCGCTTCTTGCCCTTTT  360
NF7_3     CAACGACCTAACACCAATGGCTACCAAGATATTAGCCCTCCTTGCGCTTCTTGCCCTTTT  360
L34340    CAACGACCTAACACCAATGGCTACCAAGATATTAGCCCTCCTTGCGCTTCTTGCCCTTTT  358
FF2_1     CAACGACCTAACACCAATGGCTACCAAGATATTAGCCCTCCTTGCGCTTCTTGCCCTTTT  360
FF1_1     CAACGACCTAACACCAATGGCTACCAAGATATTAGCCCTCCTTGCGCTTCTTGCCCTTTT  360
          ************************************************************

B73       AGTGAGCGCAACAAATGCGTTCATTATTCCACAGTGCTCCTAGTGCCAGTAT  420
NF7_3     AGTGAGCGCAACAAATGCGTTCATTATTCCACAGTGCTCACTGTCCTAGTGCCAGTAT  420
L34340    AGTGAGCGCAACAAATGTGTTCATTATTCCACAGTGCTCACTGTCCTAGTGCCATTAT  418
FF2_1     AGTGAGCGCAACAAATGTGTTCATTATTCCACAGTGCTCACTGTCCTAGTGCCATTAT  420
FF1_1     AGTGAGCGCAACAAATGTGTTCATTATTCCACAGTGCTCACTGTCCTAGTGCCATTAT  420
          ****************** ****************************** ***

B73       TCCACAGTTCCTCCCACCAGTTACTTCAATGGGCTTCGAACATCCAGCCGTGCAAGCCTA  480
NF7_3     TCCACAGTTCCTCCCACCAGTTACTTCAATGGGCTTCGAACATCCAGCCGTGCAAGCCTA  480
L34340    TCCACAGT CCTCCCACCAGTTACTTCAATGGGCTTCGAACATCCAGCCGTGCAAGCCTA  478
```

FIG. 1 (continued)

```
FF2_1      TCCACAGTTCCTCCCACCAGTTACTTCAATGGCTTCGAACATTCAGCCGTGCAAGCCTA 480
FF1_1      TCCACAGTTCCTCCCACCAGTTACTTCAATGGCTTCGAACATCCAGCCGTGCAAGCCTA 480
           ************************************* ******************

B73        CAGGCTACAACTAGCGCTTGCGGCGAGCGCCTTACAACAACCAATTGCCCAATTGCAACA 540
NF7_3      CAGGCTACAACTAGCGCTTGCGGCGAGCGCCTTACAACAACCAATTGCCCAATTGCAACA 540
L34340     TAGGCTACAACTAGTGCTTGCGGCGAGCGCCTTACAACAACCAATTGCCCAATTGCAACA 538
FF2_1      TAGGCTACAACTAGTGCTTGCGGCGAGCGCCTTACAACAACCAATTGCCCAATTGCAACA 540
FF1_1      TAGGCTACAACTAGTGCTTGCGGCGAGCGCCTTACAACAACCAATTGCCCAATTGCAACA 540
           ************* **********************************************

B73        ACAATCCTTGCACATCTAACCCTACAAACCATTGCAACGCAACAACAACAACAACAGTT 600
NF7_3      ACAATCCTTGCACATCTAACCCTACAAACCATTGCAACGCAACAACAACAACAACAGTT 600
L34340     ACAATCCTTGGCACATCTAACCCTACAAACCATCTAACGCAACAACGCAACAACAT---TT 595
FF2_1      ACAATCCTTGGCACATCTAACCCTACAAACCATCGAACGCAACAACAGCAACAACAG---TT 597
FF1_1      ACAATCCTTGGCACATCTAACCCTACAAACCATCGAACGCAACAACAACAACAACAG---TT 597
           ********** ********************** **********   *****      **
```

FIG. 1 (continued)

| | |
|---|---|
| B73 | TCTGCCATCACTGAGCCACCTAGCCGTGGTGAACCCTGTCACCTACTTGCAACAGCAGCT 660 |
| NF7_3 | TCTGCCATCACTGAGCCACCTAGCCGTGGTGAACCCTGTCACCTACTTGCAACAGCAGCT 660 |
| L34340 | TCTGCCATCACTGAGCCACCTAGCCAGTGGTGAACCCTGTCGCCTACTTGCAACAGCAGCT 655 |
| FF2_1 | TCTGCCATCACTGAGCCACCTAGCCGTGGTGAACCCTGTCGCCTACTTGCAACAGCAGCT 657 |
| FF1_1 | TCTGCCATCACTGAGCCACCTAGCCGTGGTGAACCCTGTCGCCTACTTGCAACAGCAGCT 657 |
| | ************************ ****************************** |
| B73 | GCTTGCATCCAACCCACTTGCTCTGGCCGAACGTAGCTGCATACCAGCAACAACAACAGCT 720 |
| NF7_3 | GCTTGCATCCAACCCACTTGCTCTGGCCGAACGTAGCTGCATACCAGCAACAACAACAGCT 720 |
| L34340 | GCTTGCATCCAACCCACTTGCTCTGGCGAACGTAGCTACATACCAGCAACAACAACAGCT 715 |
| FF2_1 | GCTTGCATCCAACCCACTTGCTCTGGCTCTGGCAAACGTAGTTGCAAACGTAGCAACAACAGCT 717 |
| FF1_1 | GCTTGCATCCAACCCACTTGCTCTGGCAAACGTAGTTGCAAACCAGCAACAACAACAGCT 717 |
| | ************************ ** * ***************** |
| B73 | GCAACAGTTTATGCCAGTGCTCAGTCAACTAGCCATGGTGAACCCTGCCGTCTACCTACA 780 |
| NF7_3 | GCAACAGTTTATGCCAGTGCTCAGTCAACTAGCCATGGTGAACCCTGCCGTCTACCTACA 780 |
| L34340 | GCAACAGTTTATGCCAGGCTCAGTCAACTAGCCATGTGAACCCTGCCGTCTACCTACA 775 |

FIG. 1 (continued)

```
FF2_1   GCAACAGTTCTGCCAGCGCTCAGTCAACTAGCCATGGTGAACCCTGCGCTACCTACA 777
FF1_1   GCAACAGTTCTGCCAGCGCTCAGTCAACTAGCCATGGTGAACCCTACGGCTACCTACA 777
        ********** *********************************  ** *********

B73     AC-------TACTTTCATCTAGCCCGCTCGCGGTGGGCAATGCACCTACGTACCTACA 831
NF7_3   AC-------TACTTTCATCTAGCCCGCTCGCGGTGGGCAATGCACCTACGTACCTACA 831
L34340  AC-------TGCTTTCATCTAGCCCGCTCGTGTGGCAATGCACCTACGTACCTACA 826
FF2_1   ACAGCAACAACTGCTTTCATCTAGCCCGCTCGTGTGGCCAATGCACCTACATACCTGCA 837
FF1_1   ACAGCAACAACTGCTTTCATCTAGCCCGCTGCTGTGCCAATGCACCTACATACCTGCA 837
        **        *  *********************  *  ***********  ** ***** **

B73     ACAACAGTTGCTGCAACAAATTGTACCAGCTCTGACTCA---GCTAGCTGTGGCAAACCC 888
NF7_3   ACAACAGTTGCTGCAACAAATTGTACCAGCTCTGACTCA---GCTAGCTGTGGCAAACCC 888
L34340  ACAACAGTTGCTGCAACAGATTGTACCAGCTCTAACTCATCAGCTAGCTATGGCAAACCC 886
FF2_1   ACAACAATTGTTGCAACAGATTGTACCAGCTCTAACTCA---GCTAGCTGTGGCAAACCC 894
FF1_1   ACAACAATTGTTGCAACATATTGTACCAGCTCTGACTCA---GCTAGCTGTGGCAAACCC 894
        ******* ** *******  *************  *****    ********** *********
```

FIG. 1 (continued)

```
B73     TGCTGCCTACTTACAACAGTTGCTTCCATTCAACCAACTGGCTGTGTCAAACTCTGCTGC 948
NF7_3   TGCTGCCTACTTACAACAGTTGCTTCCATTCAACCAACTGGCTGTGTCAAACTCTGCTGC 948
L34340  TGCTACCTACTTACAACAGTTGCTTCCATTCAACCAATTGGCTGTGTCGAACTCTGCTGC 946
FF2_1   TGCTGCCTACTTGCAACAGCTGCTTCCATTCAACCAACTGACTGTGTCGAACTCTGCTGC 954
FF1_1   TGCTGCCTACTTGCAACAGCTGCTTCCATTCAACCAACTGACTGTGTCGAACTCTGCTGC 954
        **** ******* ******  ************** **  ** ***** **********

B73     GTACCTACAACAGCGACAACAGTTACTTAATCCATTGGCAGTGGCTAACCCATTGGTCGC 1008
NF7_3   GTACCTACAACAGCGACAACAGTTACTTAATCCATTGGCAGTGGCTAACCCATTGGTCGC 1008
L34340  GTACCTACAACAGCGACAACAATTACTTAATCCATTGGCAGTGGCTAACCCATTGGTCGC 1006
FF2_1   GTACCTACAACAGCGACAACAGTTACTTAATCCATTGGCAGTGGCTAACCCATTGGTCGC 1014
FF1_1   GTACCTACAACAGCGACAACAGTTACTTAATCCACTGGCAGTGGCTAACCCATTGGTCGC 1014
        **********************************  ************************

B73     TACCTTCCTGCAGCAGCAACAATTGCTGCCATACAACCAGTTCTCTTTGATGAACCC 1068
NF7_3   TACCTTCCTGCAGCAGCAACAATTGCTGCCATACAACCAGTTCTCTTTGATGAACCC 1068
L34340  TACCTTCCTGCAGCAGCAACAA---TTGCTGCCATACAACCGTTCTCTCTTGATGAACCC 1063
```

FIG. 1 (continued)

```
FF2_1      TGCCTTCCTACAGCAGCAACAA---TTGCTGCCATACAACCAGTTCTCTTTGATGAACCC 1071
FF1_1      TGCCTTCCTACAGCAGCAACAA---TTGCTGCCATACAACCAGTTCTCTTTGATGAACCC 1071
           * ********************   ***********************************

B73        TGCCTTG------CAGCAACCCATCGTTGGAGGTGCCATCTTTTAGATTACATATGAGAT 1122
NF7_3      TGCCTTG------CAGCAACCCATCGTTGGAGGTGCCATCTTTTAGATTACATATGAGAT 1122
L34340     TGCCTTG------CAGCAACCCATCGTTGGAGGTGCCATCTTTTAGATTACATATGAGAT 1117
FF2_1      TGTCTTGTCGAGGCAGCAACCATCGTTGGAGGTGCCATCTTTTAGATTACATATGAGAT 1131
FF1_1      TGTCTTGTCGAGGCAGCAACCATCGTTGGAGGTGCCATCTTTTAGATTACATATGAGAT 1131
           ** ****       ***********************************************

B73        GTACTCGACAATGGTGCCCCTCATACCGACATGTGTTCCTAGAAATAATCAATATATTGA 1182
NF7_3      GTACTCGACAATGGTGCCCCTCATACCGACATGTGTTTCCTAGAAATAATCAATATATTGA 1182
L34340     GTACTCGACAATGGTGCCCCTCATACCGGCATGTGTTTCCTAGAAATAATCAATATATTGA 1177
FF2_1      GTACTCGATAATGGTGCCCCTCATACCGGCATGTGTTTCCTAGAAATAATCAATATATTGA 1191
FF1_1      GTACTCGATAATGGCGCCCCTCATACCGGCATGTGTTTTCTAGAAATAATCAATATATTGA 1191
           ********* ***** ***** *******************
```

FIG. 1 (continued)

```
B73     TTGAGATTTATCTCGATATATTTCTGAACTATGTTCATCATATAAATAATTGAAAACATC  1242
NF7_3   TTGAGATTTATCTCGATATATTTCTGAACTATGTTCATCATATAAATAATTGAAAACATC  1242
L34340  TTGAGATTTATCTCGATATATTTCTGAACTATGTTCATCATATAAATAACTGAAAACATC  1237
FF2_1   TTGAGATTTATCTCGATATATTTCTGAACTATGTTCATCATATAAATAATTGAAAACATC  1251
FF1_1   TTGAGATTTATCTCGATATATTTCTGAACTATGTTCATCATATAAATAATTGAAAACATC  1251
        ************************************************* **********

B73     AAATCATAATTTTAAA-CTCATGCTTGGTCAATACATAGATAATACAATATTACTTCATC  1301
NF7_3   AAATCATAATTTTAAA-CTCATGCTTGGTCAATACATAGATAATACAATATTACTTCATC  1301
L34340  AAATCATAATTTTAAAGCTCATGCTTGGTCAATACATAGATAATACAATATTACTTCATC  1297
FF2_1   AAATCGTAATTATAAA-CTCATGCTTGGTCAATACATAGATAATACAATATTACTTCATC  1310
FF1_1   AAATCGTAATTATAAA-CTCATCCTTGGTCAATACATAGATAATACAATATTACTTCATC  1310
        ***** ***** **** ***** *************************************

B73     ATCCCAATGATGTCCTAGCCCAACCTATTGAATGTTAATGTTTGGTTGTGTGAGGGTGTG  1361
NF7_3   ATCCCAATGATGTCCTAGCCCAACCTATTGAATGTTAATGTTTGGTTGTGTGAGGGTGTG  1361
L34340  ATCCCAATGATGTCCTAGCACAACCTATTGAATGTTAATGTTTGGTTGTGTGGGGGTGTG  1357
```

FIG. 1 (continued)

```
FF2_1    ATCCCAATGATGTCCTAGCACAACCTATTGAATGTTAATGTTTGGTTGTGTGAGGGTGTG  1370
FF1_1    ATCCCAATGATGTCCTAGCCCAACCTATTGAATGTTAATGTTTGGTTGTGTGAGGGTGTG  1370
         ****************** ********************************** *******

B73      TTTATAACATAGATGTGATTATTTGCGCTTTTTGTTGAGTATATACATATATGGTATGTT  1421
NF7_3    TTTATAACATAGATGTGATTATTTGCGCTTTTTGTTGAGTACATACATATATGGTATGTT  1421
L34340   TTTATAACATAGATGTGATTATTTGTGCTTTTTGTTGAGTATATACATATATGGTATGTT  1417
FF2_1    TTTATAACATAGATGTGATTATTTGCGCTTTTTGTTGAGTACATACATATATGGTATGTT  1430
FF1_1    TTTATAACATAGATGTGATTATTTGCGCTTTTTGTTGAGTACATACATATATGGTATGTT  1430
         *********************** * ************** *****************

B73      GATTTGATATAGTGATGGACACATGCTTTGGCCTTGGATATTCAAATCACTTGTACTTGC  1481
NF7_3    GATTTGATATAGTGATGGACACATGCTTTGGCCTTGGATATTCAAATCACTTGTACTTGC  1481
L34340   GATTTGATATAGTGATGGACACATGCTTTGGCCTTGGATATTCAAATCACTTGTACTTGC  1477
FF2_1    GATTTGATATAGTGATGGACACATGCTTTGACCATGAATATTCAAATCAGTTGTACTTGC  1490
FF1_1    GATTTGATATAGTGATGGACACATGCTTTGACCATGAATATTCAAATCAGTTGTACTTGC  1490
         ****************************** ** ** ********* **********
```

FIG. 1 (continued)

| | |
|---|---|
| B73 | ACGAAGCAAAACATAATATAAGTTTAGAAGTAAACTTGTAACTATGTCCAAACATGCTCA 1541 |
| NF7_3 | ACGAAGCAAAACATAATATAAGTTTAGAAGTAAACTTGTAACTATGTCCAAACATGCTCA 1541 |
| L34340 | ACGAAGCAAAACATAATATAAGTTTAGAAGTAAACTTGTAACTGTGTCCAAACATGCTCA 1537 |
| FF2_1 | ACGAAGCAAAACATAATATAAGTTTAGGAGTACACTTATAACTGTGTCCAAACATGCTCA 1550 |
| FF1_1 | ACGAAGCAAAGCATAACATAAGTTTAGGAGTAGACTTATAACTATGTCCAAACATGCTCA 1550 |
| | ******* ***** ************ **** ***** * ************* |
| B73 | CACAAAGTCATACCGCATTATAATTTTTTGGTAAATATTCAACACATGTATTTTTACAA 1601 |
| NF7_3 | CACAAAGTCATACCGCATTATAATTTTTTGGTAAATATTCAACACATGTATTTTTACAA 1601 |
| L34340 | CACAAAGTCATATCGCATTATATT-TTTTGGTAAATATTCAACACATGTATTTTTACAA 1597 |
| FF2_1 | CACAAATTCATACCACCATTATAATTTTTTGGTAAATATTCCACACATGTATTTTTACAA 1610 |
| FF1_1 | CACAAATTCATACCACCATTATAATTTTTTGGTAAATATTCCACACATGTATTTTTACAA 1610 |
| | ****** ***** * ******** ************ ************** |
| B73 | GAACCCAAATTTTACAGACAAATGCAGCATTGTAGACATGTAGAATTCTTTGAAGCATGT 1661 |
| NF7_3 | GAACCCAAATTTTACAGACAAATGCAG-CATTGTAGACATGTAGAATTCTTTGAAGCATGT 1661 |
| L34340 | GAACCCAAATTTTACAGACAAATGCAG-CATTGTAGACATGTAGAATTCTTTGAAGCATGT 1657 |

FIG. 1 (continued)

FF2_1    GAACCCAAATTTACAGACAAATGCAGCATTGTAGACATGTAGAATTCTTTCAAGCATGT 1670
FF1_1    GAACCCAAATTTACAGACAAATGCAGCATTGTAGACATGTAGAATTCTTTCAAGCATGT 1670
         *********************************************************

B73      GAACTTAACAACACCAA 1678
NF7_3    GAACTTAACAACACCAA 1678
L34340   GAACTTAACAACACCAA 1674
FF2_1    GAACTTAACAACACCAA 1687
FF1_1    GAACTTAACAACACCAA 1687
         *****************

FIG. 2

```
B73(SEQ ID NO:9)    -21 MATKILALLALLALLVSATNAFIIPQCSLAPSASIPQFLPPVTSMGFEHPAVQAYRLQLA  39
NF7_3(SEQ ID NO:13)     MATKILALLALLALLVSATNAFIIPQCSLAPSASIPQFLPPVTSMGFEHPAVQAYRLQLA
L34340(SEQ ID NO:10)    MATKILALLALLALLVSATNVFIIPQCSLAPSAIIPQFLPPVTSMGFEHPAVQAYRLQLV
FF2_1(SEQ ID NO:11)     MATKILALLALLALLVSATNVFIIPQCSLAPSAIIPQFLPPVTSMGFEHPAVQAYRLQLV
FF1_1(SEQ ID NO:12)     MATKILALLALLALLVSATNVFIIPQCELAPSAIIPQFLPPVTSMGFEHPAVQAYRLQLV
                        *******************:*****:*****:*********************** :

B73      LAASALQQPFAQLQQQSLAHLTLQTIATQQQQQFLPSLSHLAVVNPVTYLQQQLLASNP  99
NF7_3    LAASALQQPIAQLQQQSLAHLTLQ-IATQCQQQQFLPSLSHLAVNPVTYLQQQLLASNP
L34340   LAASALQQPIAQLQQQSLAHLTLQ-IATQQQQ-HFLPSLSHLAVVNPVAYLQQQLLASNP
FF2_1    LAASALQQPIAQLQQQSLAHLTLQ-IATQQQQ-QFLPSLSHLAVVNPVAYLQQQLLASNP
FF1_1    LAASALQQPIAQLQQQSLAHLTLQ-IATQQQQ-QFLPSLSHLAVVNPVAYLQQQLLASNP
         *********:************* ******   :*******:***** *********

B73      LALANVAAYQQQQLQQQLQQFMPVLSQLAMVNPAVYLQ----LLSSSPLAVGNAPTYLQQQLLQ  157
NF7_3    LALANVAAYQQQQLQQQLQQFMPVLSQLAMVNPAVYLQ----LLSSSPLAVGNAPTYLQQQLLQ
L34340   LALANVATYQQQQLQQQLQQFMPALSQLAMVNPAVYLQ----LLSSSPLAVGNAPTYLQQQLLQ
```

FIG. 2 (continued)

```
FF2_1      LALANVVANQQQQLQQFLPALSQLAMVNPAAYLQQQLLSSSPLAVANAPTYLQQQLLQ
FF1_1      LALANVVANQQQQLQQFLPALSQLAMVNPTAYLQQQQLLSSSPLAVANAPTYLQQQLLQ
           ******..********:*.************..***..*********.**********

B73        QIVPALT-QLAVANPAAYLQQLLPFNQLAVSNSPAYLQQRQQLLNPLAVANPLVATFLQQ 216
NF7_3      QIVPALT-QLAVANPAAYLQQLLPFNQLAVSNSPAYLQQRQQLLNPLAVANPLVATFLQQ
L34340     QIVPALTHQLAMANPATYLQQLLPFNQLAVSNSAAYLQQRQQLLNPLAVANPLVATFLQQ
FF2_1      QIVPALT-QLAVANPAAYLQQLLPFNQLTVSNSAAYLQQRQQLLNPLAVANPLVAAFLQQ
FF1_1      HIVPALT-QLAVANFAAYLQQLLPFNQLTVSNSAAYLQQRQQLLNPLAVANPLVAAFLQQ
           :******5*:*:*6*********:*:***********:.**

B73        QQQLLPYNQFSLMNEAL--QQPIVGGAIF 243
NF7_3      QQQLLPYNQFSLMNFAL--QQPIVGGAIF
L34340     QQ-LLPYNQFSLMNFAL--QQFFVGGAIF
FF2_1      QQ-LLPYNQFSLMNFVLSRQQFFVGGAIF
FF1_1      QQ-LLPYNQFSLMNFVLSRQQFFVGGAIF
           7***********.*  ***********
```

FLOURY 2 GENE-SPECIFIC ASSAY IN MAIZE FOR FLOURY (FL2) TRAIT INTROGRESSION

CROSS-REFERENCE TO RELATED APPLICATIONS

This application is a national stage entry under 35 U.S.C. § 371 (b) of PCT International Application No. PCT/US2013/042997, filed May 29, 2013, and claims priority under 35 U.S.C. § 119(e) to U.S. Provisional Application Ser. No. 61/653,287, filed May 30, 2012, the disclosures of both which are hereby incorporated by reference in their entirety.

INCORPORATION BY REFERENCE OF MATERIAL SUBMITTED ELECTRONICALLY

Incorporated by reference in its entirety is a computer-readable sequence listing submitted concurrently herewith and identified as follows: one 28,672 byte ASCII (text) file named "223450_SEQ_LISTING_ST25.txt", created on May 28, 2013.

FIELD OF THE DISCLOSURE

The disclosure relates generally to plant breeding. Methods are provided for determining the presence of the fl2 mutation and the zygosity of plants for this mutation. Methods of the disclosure are useful for selecting for plants bearing the floury2 (fl2) trait and for fl2 trait introgression into plants, such as maize.

BACKGROUND

Corn silage is a popular forage for ruminant animals because of its high energy and digestibility. Corn grain is often added to ration formulations to improve nutritional balance. Kernel hardness and texture play an important role in starch digestibility. A softer kernel or a hybrid that is harvested when it is less mature is easier to digest in the rumen. Naturally-occurring maize mutations, such as brown midrib (BMR), floury2 (fl2), and opaque2 (O2) have become a focus of silage product development because they are associated with a softer kernel. BMR germplasms, for example, have reduced cell wall lignin content. Cherney et al. (1991) Adv. Agron. 46:157-98. Plants with the fl2 or O2 mutations produce soft, starchy endosperm with irregularly shaped protein bodies and higher lysine content than wild type. Coleman et al. (1997) PNAS 94:7094-97. Adding grain with the fl2 or O2 mutations to rations may increase digestibility in ruminants, reducing the amount of grain needed for nutritional requirements and reducing the need for kernel processing at harvest. See Ladely et al. (1995) J. Anim. Sci. 73:228-235.

The floury2 trait is reportedly associated with a mutation in one of the members of the zein gene family, the major prolamin storage proteins in maize seed. Song et al. (2001) Gen. Res. 11:1817-25. Introgression of the fl2 mutation into corn lines is a time-consuming process. Since the fl2 mutant allele is semidominant, phenotyping based on kernel vitreousness is difficult and often ambiguous. Coleman et al. (1997). A rapid, gene-specific molecular assay is needed to detect the fl2 mutant allele and determine zygosity in candidate plants. This assay will greatly facilitate breeding efforts by reducing the time needed to select plants with desirable features.

SUMMARY OF THE DISCLOSURE

Described herein are methods for high-throughput PCR-based molecular characterization of floury2 corn varieties (e.g., fl2 mutants) that may greatly enhance the breeding process for introgression of corn lines containing fl2. Disclosed are methods for determining the zygosity of a plant tissue sample, and hence the plant from which the sample was prepared, by determining the presence or absence of an fl2 mutant and the wild type alpha-zein alleles. Thus, a fluorescent probe PCR-based zygosity assay (referenced herein as the KASPar® assay) is provided that specifically detects and tests the zygosity status at the fl2 locus and is capable of distinguishing a unique SNP variant in the gene between segregating populations. Also disclosed is the nucleotide sequence comprising this unique SNP, and plants and germplasm selected using these methods.

In a particular embodiment, a method for determining the zygosity and/or presence/absence of an allele using corn plant tissue includes: obtaining a sample of isolated genomic DNA from the corn plant tissue; contacting the isolated genomic DNA with at least one nucleic acid molecule comprising a nucleotide sequence capable of hybridizing to SEQ ID NO:9 under high stringency conditions and at least one nucleic acid molecule capable of hybridizing to SEQ ID NO:10 under high stringency conditions; and determining zygosity of a fl2 mutation in the isolated genomic DNA.

In another embodiment, a method for reliably and predictably introgressing a trait for high lysine content into plant germplasm includes: crossing a plant having a mutation in the fl2 gene with another plant; obtaining a sample of isolated genomic DNA from a progeny plant produced by the cross; contacting the isolated nucleic acid with at least one nucleic acid molecule having a nucleotide sequence capable of hybridizing to SEQ ID NO:10 under high stringency conditions; and selecting progeny from the cross that includes a mutation in the fl2 gene by reproducing a plant from which a sample was obtained that binds at least one nucleic acid molecules with high stringency, thereby producing a genetically engineered plant wherein a trait for high lysine content that has been introgressed into the germplasm of the genetically engineered plant.

BRIEF DESCRIPTION OF THE FIGURES

FIG. 1 shows the alignment of the 22 kDa α-zein genomic sequences from the wild-type corn line B73 (B73), wild-type corn line 1 (NF7_3), L3430 is a publicly available floury2 corn line 1 (L3430), floury2 corn line 2 (FF1_1) and floury2 corn line 3 (FF2_1). 72 SNPs and 7 InDels are identified.

FIG. 2 shows the alignment of the predicted 22-kDa α-zein protein sequences from B73, wild-type corn line 1 (NF7_3), floury2 corn line 1 (L3430), floury2 corn line 2 (FF1_1) and floury2 corn line 3 (FF2_1). The lighter color font indicates the A to V substitution at the −1 signal peptide.

SEQUENCE LISTING

Figure 3:
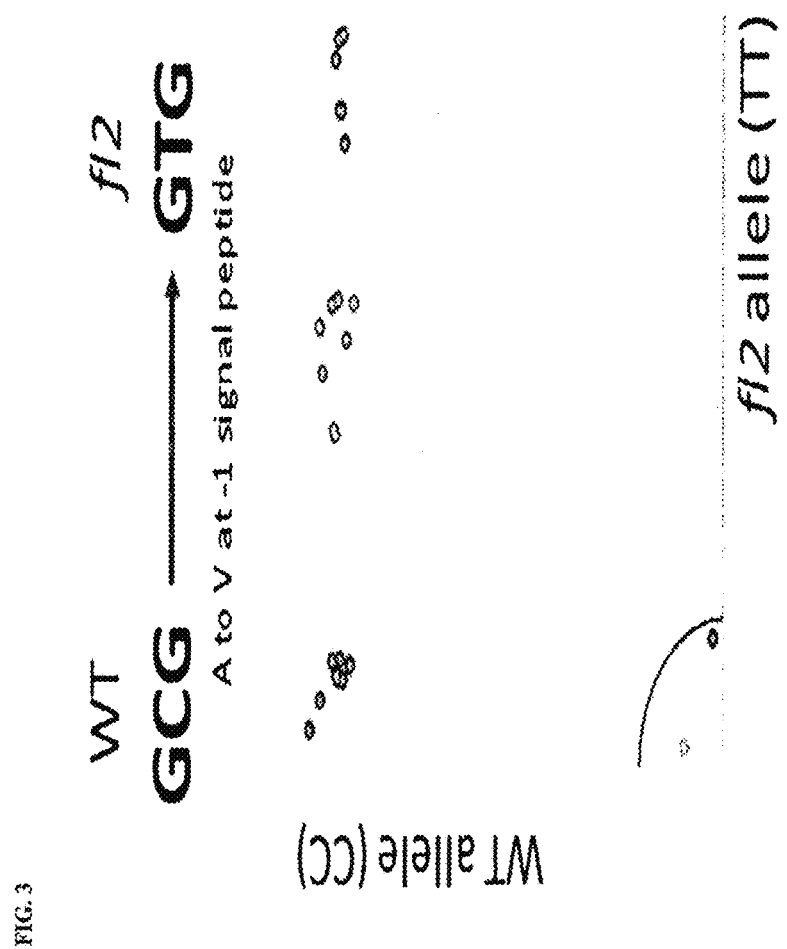
FIG. 3 shows the KLIMS Data analysis of 23 maize inbred lines genotyped with KASPar® assay (FAM signal for mutant allele as x-axis and CAL signal for wild type allele as y-axis) based on the alanine to valine substitution on −1 signal peptide.

The nucleic acid sequences listed in the accompanying sequence listing are shown using standard letter abbreviations for nucleotide bases, as defined in 37 C.F.R. § 1.822. Only one strand of each nucleic acid sequence is shown, but the complementary strand is understood as being included by any reference to the displayed strand. In the accompanying

SEQUENCE LISTING

SEQ ID NO:1 shows a forward primer sequence (Zein_68F) used to amplify the 22 kDa B73 α-zein gene: GAGATCATGCATGTCATTCCA.

SEQ ID NO:2 shows a reverse primer sequence (Zein_68R) used to amplify the 22 kDa B73 α-zein gene: TTGGTGTTGTTAAGTTCACATGC.

SEQ ID NO:3 shows an oligonucleotide sequence (Zein_513F) from the α-zein gene used to sequence a B73 α-zein partial gene: AATCCTTGGCACATCTAA.

SEQ ID NO:4 shows an oligonucleotide sequence (Zein-23R) from the α-zein gene used to sequence a B73 α-zein partial gene: TAGGTGGCTCAGTGATGGCAGAA.

SEQ ID NO:5 shows an oligonucleotide sequence (385_R) from the α-zein gene used to sequence a B73 α-zein partial gene: CTAAAAGATGGCACCTCCAA.

SEQ ID NO:6 shows an allele-specific primer sequence (A1).

SEQ ID NO:7 shows an allele specific primer sequence (A2).

SEQ ID NO:8 shows a common (reverse) primer sequence (C1).

SEQ ID NO:9 shows the nucleotide sequence of the 22 kDa α-zein gene from plant line B73.

SEQ ID NO:10 shows the nucleotide sequence of the 22 kDa α-zein gene from plant line L34340.

SEQ ID NO:11 shows the nucleotide sequence of the 22 kDa α-zein gene from plant line FF2_1.

SEQ ID NO:12 shows the nucleotide sequence of the 22 kDa α-zein gene from plant line FF1_1.

SEQ ID NO:13 shows the nucleotide sequence of the 22 kDa α-zein gene from plant line NF7_3.

SEQ ID NO:14 shows the predicted amino acid sequence of the α-zein gene from plant line B73.

SEQ ID NO:15 shows the predicted amino acid sequence of the α-zein gene from plant line L34340.

SEQ ID NO:16 shows the predicted amino acid sequence of the α-zein gene from plant line FF2_1.

SEQ ID NO:17 shows the predicted amino acid sequence of the α-zein gene from plant line FF1_1.

SEQ ID NO:18 shows the predicted amino acid sequence of the α-zein gene from plant line NF7_3.

SEQ ID NO:19 shows the primer sequence A1-1.
SEQ ID NO:20 shows the primer sequence A2-1.
SEQ ID NO:21 shows the primer sequence C1-1.
SEQ ID NO:22 shows the primer sequence A1-2.
SEQ ID NO:23 shows the primer sequence A2-2.
SEQ ID NO:24 shows the primer sequence C1-2.
SEQ ID NO:25 shows the primer sequence A1-3.
SEQ ID NO:26 shows the primer sequence A2-3.
SEQ ID NO:27 shows the primer sequence C1-3.
SEQ ID NO:28 shows the primer sequence A1 4.
SEQ ID NO:29 shows the primer sequence A2-4.
SEQ ID NO:30 shows the primer sequence C1-4.
SEQ ID NO:31 shows the primer sequence A1-5.
SEQ ID NO:32 shows the primer sequence A2-5.
SEQ ID NO:33 shows the primer sequence C1-5.
SEQ ID NO:34 shows the primer sequence A1-6.
SEQ ID NO:35 shows the primer sequence A2-6.
SEQ ID NO:36 shows the primer sequence C1-6.

DETAILED DESCRIPTION

I. Overview of Several Embodiments

Disclosed herein are methods for PCR-based gene-specific molecular assays to detect the presence of the floury2 (fl2) trait in maize.

In embodiments herein, the method may disclose a method to determine the zygosity of the plant for fl2 mutant alleles.

Embodiments herein describe the cloning of the α-zein gene from multiple maize lines. In some embodiments, several mutations associated with the floury phenotype are identified.

In a preferred embodiment, a gene-specific assay for the fl2 trait is described. In particular embodiments, a method for using the fl2 gene specific assay to select plant germplasm is described.

In some embodiments, a method for using a fl2 gene specific assay to facilitate introgression of the fl2 mutant gene is described. The introgression of fl2 is not as complicated as O2.

II. Abbreviations
BMR brown midrib mutation
fl2 floury2 mutation
O2 opaque2 mutation
PCR polymerase chain reaction
III. Terms
Base position: A "base position," as used herein, refers to the location of a given base or nucleotide residue within a designated nucleic acid. The designated nucleic acid may be defined by alignment (see below) with a reference nucleic acid.

Elite line: As used herein, the term "elite line" means any line that has resulted from breeding and selection for superior agronomic performance. An elite plant is any plant from an elite line.

Introgression: As used herein refers to a genomic segment that has moved from one individual, species, variety or cultivar into the genome of another individual, species, variety or cultivar, by crossing those individuals, species, varieties or cultivars. As used herein, the terms "introgressing", "introgress" and "introgressed" refer to both a natural and artificial process whereby individual genes or entire traits are moved from one individual, species, variety or cultivar into the genome of another species, variety or cultivar, by crossing those species, varieties or cultivars. In plant breeding, the process usually involves selfing or backcrossing to the recurrent parent to provide for an increasingly homozygous plant having essentially the characteristics of the recurrent parent in addition to the introgressed gene or trait.

Line: As used herein, a "line" or a "plant line" refers to a group of plants that display little genetic variation (e.g., no genetic variation) between individuals for at least one trait. Inbred lines may be created by several generations of self-pollination and selection or, alternatively, by vegetative propagation from a single parent using tissue or cell culture techniques. As used herein, the terms "cultivar," "variety," and "type" are synonymous, and these terms refer to a line that is used for commercial production.

Nucleic acid molecule: As used herein, the term "nucleic acid molecule" (or "nucleic acid" or "polynucleotide") may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The term may refer to a molecule of RNA or DNA of indeterminate length. The term includes single- and double-stranded forms of DNA. A nucleic acid molecule may include either or both naturally-occurring and modified nucleotides linked together by naturally occurring and/or non-naturally occurring nucleotide linkages.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA, Oligonucleotides composed of DNA (oligodeoxyribonucleotides) may be used in PCR, a technique for the amplification of small DNA sequences. In PCR, the oligonucleotide is typically referred to as a "primer," which allows a DNA polymerase to extend the oligonucleotide and replicate the complementary strand.

Sequence identity: The term "sequence identity" or "identity," as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences, amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

Single-nucleotide polymorphism (SNP): As used herein, the term "single-nucleotide polymorphism" may refer to a DNA sequence variation occurring when a single nucleotide in the genome (or other shared sequence) differs between members of a species or paired chromosomes in an individual.

Trait or phenotype: The terms "trait" and "phenotype" are used interchangeably herein. For the purposes of the present disclosure, a trait of particular interest is seed coat color. Some canola varieties exhibit a yellow seed coat, while further varieties exhibit a dark (e.g., black, dark, and mottled) seed coat.

Zein: As used herein, the term "zein" shall refer to any member of a class of genes, and their gene products, gene fragments, partial genes, protein products, and RNA products, in or derived from the zein superfamily in maize and other plants. Zeins may include the following known classes or family members: α-zeins, β-zeins, γ-zeins and δ-zein. In embodiments, the α-zein gene, gene segment, partial gene, or its protein or RNA products is referenced.

Zygosity: As used herein, the term "zygosity" refers to the similarity, or lack thereof, of alleles of a gene for an inherited trait in an organism. If both alleles are the same, the organism is "homozygous" for the trait. If both alleles are different, the organism is "heterozygous" for that trait. If one allele is missing, it is "hemizygous." If both alleles are missing, it is "nullizygous."

Unless otherwise specifically explained, all technical and scientific terms used herein have the same meaning as commonly understood by those of ordinary skill in the art to which this disclosure belongs. Definitions of common terms in molecular biology can be found in, for example, Lewin B., *Genes V*, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8).

Unless indicated otherwise, the terms "a" and "an" as used herein refer to at least one.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

IV. Gene-specific molecular assay for genotype and zygosity determination of fl2

A. Overview

Described herein is a gene-specific molecular assay for characterizing the floury2 (fl2) trait in plants. Particular examples utilize the KASPar® PCR-based assay system to detect specific fl2 mutations, and compare to the corresponding wild-type sequences in the same assay. In some examples, the zygosity of the plant may be determined by the presence or absence of an fl2 mutant allele and the wild-type α-zein allele. Particular examples describe a unique alanine to valine substitution at the 39 amino acid position, which may be used for molecular characterization. This assay can differentiate the fl2 mutant allele from the wild type allele and has been confirmed with segregating populations. In examples, the assay may be used for introgression of a desired trait, such as the floury2 trait, into plant lines bearing other desirable features. This gene-based marker/assay will be a powerful tool for accelerating molecular breeding processes with fl2.

B. Floury2 (fl2) corn

Zeins are the major prolamin storage proteins in maize seeds synthesized starting between 10 and 45 days after pollination, and represent 60-70% of total seed protein. Coleman et al. (1997); Kodrzycki et al. (1989) Plant Cell 1:105-114. Wild type zein proteins are glutamine and proline rich, but deficient in lysine and tryptophan, making the grain nutritionally inferior, especially for monogastric animals. Coleman (1995) PNAS 92:6828-31.

Four distinct classes of zein proteins have been named, classified as α-, β-, γ-, and δ-zein. Coleman et al. (1997). The alpha zeins, the most abundant class, are 19 and 22 kDa. Hagen and Rubenstein (1981) Gene 13(3):239-49. Song et al. isolated and sequenced all 23 members of the maize 22 kDa alpha zein gene family. (2001) Gen. Res. 11:1817-25. Twenty-two of the α-zein genes are located in a tandem array on the short arm of chromosome 4S, with the twenty-third gene located at a more proximal location on the same chromosome. Song (2001). Only seven of these genes are reportedly expressed, based on cDNA profiles, with the expressed genes interspersed among the nonexpressed genes. Song (2001).

The floury2 (fl2) and opaque2 (O2) traits in maize are associated with a softer kernel, almost twice the lysine content of normal maize, and increased digestibility in ruminants and chickens. Nelson et al. (1965) Science 150: 1469-70. Chickens fed with fl2 corn grow faster. Cromwell et al. (1968) Poul. Sci. 57:840-47. Calves fed a high lysine corn diet are 10% more efficient and degrade crude protein as much as 27% faster than calves fed normal corn. Ladely et al. (1995) J. Anim. Sci. 73:228-35. Because of its soft kernel, floury2 seeds are subject to mechanical damage, making them susceptible to insect and fungal stresses, but introgression of the fl2 allele into plant lines bearing other desirable features may alleviate this problem.

The floury2 phenotype is caused by mutations in the zein gene family. Coleman et al. (1997) PNAS 94:7094-97. The wild type allele associated with the fl2 mutation is one of the expressed alpha zein genes. Coleman et al. identified an alanine to valine substitution at the −1 position of the signal peptide (a [T/C] SNP) in the maize 22-kDa alpha zein gene thought to be responsible for the fl2 mutation. (1995 and 1997). The signal peptide normally targets the alpha zein protein to the lumen of the rough endoplasmic reticulum (RER). The mutation prevents cleavage of the signal peptide and results in a mature protein that is 2 kDa larger than expected. The defective 24 kDa protein triggers improper assembly and packaging of zein family proteins during endosperm development, leading to a reduction in prolamin storage protein synthesis and an accumulation of lysine. Coleman et al. (1997).

C. Phenotypic selection for floury2 trait

Breeders have attempted to introduce the fl2 and O2 mutations into high performance BMR lines, but selecting for these mutants is complicated. Vitreousness can be used to phenotypically select for mutations that influence the opacity of the maize kernel, including the fl2 and O2 mutations. Unfortunately, vitreousness is also affected by the morphology and natural discoloration of the kernel, making phenotypic characterization using a light box time-consuming and often misleading. Phenotypic selection for O2 is also complicated by the presence of multiple modifier genes. Holding et al. (2010) Theor. App. Gen. 122:783-94. The fl2 mutant allele is semi-dominant, with the severity of the phenotype determined by the number of copies of the mutant allele. Maize endosperm contains two copies of genetic material from the female parent and one copy from the male parent. The phenotype of progeny seeds thus varies significantly, depending on which parent the fl2 mutant allele comes from.

D. Molecular detection assay

Gene-specific molecular assays for the BMR and fl2 traits would greatly facilitate programs to produce low lignin and soft kernel silage by improving selection accuracy and decreasing the breeding cycle. A gene-specific assay has previously been developed for brown midrib 1 (bm1) and brown midrib 3 (bm3), but no gene-specific assay was previously available for the fl2 mutation.

In experiments, the 22-kDa α-zein gene was cloned and sequenced from two floury2 donors originated from the J15 and Oh-43 lines, as well as a wild type maize inbred line. The SNP mutation at the −1 position was confirmed and zygosity assays were designed. However, this assay failed to differentiate mutants from the wild type due to the high homology of the zein family genes. A unique alanine to valine substitution at the 39 amino acid position was found. A molecular assay was designed targeting the associated SNP and was found to be useful for differentiating the fl2 mutant allele from the wild type allele. The validity of the assay was confirmed with segregating populations.

Described herein is a gene specific KASPar® PCR assay, generally useful for zygosity analysis of fl2 corn or putative fl2 corn. In particular embodiments, a gene (allele) specific KASPar® PCR assay may be used to analyze the zygosity of corn for as fl2 mutation. In embodiments, the gene specific assay may provide a high throughput system and method for rapidly screening plants for a selected genotype including, for example, the floury2 (fl2) trait. In some of these embodiments, for example, a microarray system or well plate containing 96, 384 or 1536 well samples may be assayed simultaneously.

Primers and probes for use in a gene specific KASPar® PCR assay may be designed based on a known mutation in the gene of interest. The mutation may be, for example, a single nucleotide polymorphism (SNP) or an insertion or deletion mutation. In certain embodiments, primers and probes for an fl2-specific assay may be designed based on a SNP (C/T) at nucleotide 495 that is associated with a substitution from alanine to valine at the −1 signal peptide of the fl2 gene. In a preferred embodiment, primers and probes may be designed based on a SNP associated with an alanine to valine substitution at the 39 amino acid position of the gene. In some embodiments, the gene specific KASPar® PCR assay may target other mutations that may be associated with a trait of interest, such as the floury2 trait.

In embodiments, two allele-specific primers may be used with a single common (reverse) primer to selectively amplify an allele-specific fragment of the fl2 gene. In some embodiments, an fl2-specific assay amplifies a fragment that is unique to one allelic form of fl2, such as the allele bearing the C/T SNP at position 495. In certain embodiments, a target-specific oligonucleotide probe hybridizes under high stringency conditions to a target sequence in a genomic DNA sample between two PCR primers.

Target-specific oligonucleotides may be labeled, for example, with fluorescent dyes (e.g., FAM, VIC, and MGB-NFQ), which may allow rapid quantification of a target-specific fluorescent signal. PCR products may be measured after a pre-determined number of cycles, for example, when the reaction is in the early exponential phase. Negative control samples may comprise genomic DNA from any corn variety, for example, without an fl2 mutation. Positive control samples may comprise genomic DNA from a corn variety with a known fl2 mutation. Control hemizygous samples may comprise either genomic DNA from a corn variety predetermined to be hemizygous for an fl2 mutation; or a hemizygous sample may comprise equal proportions of negative control DNA to DNA from a corn variety predetermined to be homozygous for fl2.

DNA may be isolated (for example, extracted, and purified) from corn plant tissue by methods known to those of skill in the art. Commercial kits for DNA isolation are available, for example, from Qiagen, Inc. In some embodiments, leaf discs from a particular plant are punched and transferred into collection tubes. The puncher may be cleaned after each sampling with 70% alcohol, rinsing in water, and drying. DNA extraction buffers may be prepared according to the manufacturer's recommendations. DNA may then be isolated using the kit according to the manufacturer's instructions. Finally, the concentration of the isolated DNA may be determined using, for example, a Quant-iT™ PicoGreen® Quantfication Kit (Invitrogen, Carlsbad, Calif.) and a spectrophotometer, or by any other suitable technique.

Once primers, probes, and genomic DNA sample(s) have been prepared or otherwise made available, a competitive allele specific PCR (KASPar®) assay may be designed using commercial software, such as Dow AgroSciences Kraken workflow manager, available through KBiosciences (KBiosciences, Hoddesdon, Hertfordshire, UK) to identify nucleic acid sequences of interest (e.g., sequences particular to a fl2 mutation) in the genomic DNA sample(s). In particular embodiments, individual PCR reaction mixtures are prepared that contain all the reaction components, except the genomic DNA sample(s). For a KASPar® reaction comprising primers and gene-specific probes for fl2 mutant and wild-type corn, the reaction mixture may comprise an assay mix containing two allele-specific (forward) primers, a common (reverse) primer, buffer, reaction mix, 50 mM $MgCl_2$, and water. To this mix may be added genomic DNA, and PCR cycles may be initiated according to standard protocols to amplify fragments of interest.

In some embodiments, a PCR (e.g. KASPar®) assay can be set up with appropriate controls. For example, a reaction in a multi-well plate may be performed with control wells comprising: (1) negative control(s) with reagents but no DNA sample; (2) homozygous positive control(s) comprising fl2 corn genomic DNA; (3) and hemizygous positive control(s), as described above. DNA is then amplified by PCR under suitable cycle conditions. For example, in some embodiments using a GenAmp® PCR System 9700, there may be a single initial denaturation cycle at 94° C. for 15 minutes, then 20 cycles of denaturation (94° C. for 10 seconds) and annealing (57° C. for 5 seconds) and extension (72° C. for 40 seconds), followed by 22 additional cycles with longer annealing (denaturation at 94° C. for 10 seconds; annealing at 57° C. for 20 seconds, extension at 72° C. for 40 seconds). Those of skill in the art understand that PCR cycle conditions may be varied according to the practitioner's discretion or the specific primer/oligonucleotide sequences involved, and comparable results obtained.

E. Determination of genotype and/or zygosity for the floury 2 (fl2) trait

A gene-based (allele-specific) molecular assay may be used for genotype and/or zygosity analysis of plants. In some embodiments, a unique SNP may be targeted using a KASPar® PCR-based assay system. In a preferred embodiment, the SNP that is targeted may be associated with an alanine to valine substitution at the 39 amino acid position of the 22 kDa α-zein gene. For assays using the KASPar® method, PCR products may be analyzed using fluorometric detection. For example, a fluorescent dye may be measured with an excitation wavelength at 485 nm and emission wavelength at 520 nm for fluorescent signal of FAM and 520 nm and 560 nm for CAL.

Following the completion of the PCR reaction and probe detection, a table and distribution graph may be generated using, for example, any suitable computer graphics software. Results obtained with wild-type, hemizygous and homozygous DNA of similar and/or known genotypic backgrounds may serve as positive or negative controls. In a segregating population, three clusters of data points may be obtained, allowing the visual determination of a sample result as likely belonging to one of the segregated clusters. Alternatively, data analysis computer software may be used to calculate the probability that a sample result belongs to each segregated cluster, with the most probable cluster serving as the sample designation. When a visual determination is made, the boundary of each cluster may be arbitrary, for example, when three clusters of data points are clearly visible.

Raw fluorescence intensity data may also be analyzed directly from a plate reader using a suitable analysis package, such as KLIMS (KBioscience laboratory information management system). A graph with the relative fluorescence units (RFU) of a fluorescence signal generated by a specific probe for a mutant allele plotted on one axis, and the RFU of a fluorescence signal generated by a specific probe for the wild-type allele plotted on the other axis may be generated. Zygosity determinations may then be made based on the cluster separation in a graphical display of the data.

Samples that do not contain mutant genomic DNA (e.g., a BMR mutation) may only result in fluorescence readings of the wild-type PCR product. Samples containing hemizygous or homozygous mutant genomic DNA may result in RFU readings for the mutant-specific probe higher than that of a negative background control. If a sample yields no adequate results, the genomic DNA in the sample may not be of adequate quality and/or quantity, and a new DNA preparation and/or new PCR reaction should be performed. Preferably, a negative control sample containing no DNA sample shows very low detection of gene-specific probe(s). It is also preferable that known homozygous controls show only high detection of the mutant or wild-type DNA in the control, and that known hemizygous controls show both high detection of the mutant and wild-type DNA.

A "test run" of the PCR method and genotype and/or zygosity determination may be performed with all appropriate controls prior to screening of samples. Further optimization of the methods may be desirable for components that may differ among uses (e.g., method of genomic DNA preparation, Taq DNA polymerase, oligonucleotides, laboratory equipment, etc.). PCR and thermal cycling conditions may be established that amplify both mutant and/or wild-type sequences in a known genomic DNA template with acceptable levels of probe detection (e.g., acceptable RFU for fluorescently labeled oligonucleotide probes).

VI Introgression of a trait for high lysine content into plant germplasm

Introgression of a desirable trait in plants may be facilitated by repeated backcrossing.

Described herein are methods for producing a corn plant with high lysine content (e.g., fl2 corn), through conventional plant breeding involving sexual reproduction. Methods may comprise crossing a first parent corn plant that comprises in its genome at least one copy of a fl2 mutation to a second parent corn plant, so as to produce $F_1$ progeny. The first plant can be any fl2 corn plant or varieties including, for example, Oh-43 or J15. The second parent corn plant can be any corn plant that is capable of producing viable progeny corn plants (i.e., seeds) when crossed with the first corn plant. The first and second parent corn plants may be of the same corn species (e.g., Zea mays (maize)). The methods may further involve selfing the $F_1$ progeny to produce $F_2$ progeny. Methods may further involve one or more generations of backcrossing the $F_1$ or $F_2$ progeny plants to a plant of the same line or genotype as either the first or second parent corn plant. Alternatively, the $F_1$ progeny of the first cross, or any subsequent cross, can be crossed to a third corn plant that is of a different line or genotype than either the first or second plant.

In some embodiments, progeny plants are subjected to a genotype and/or zygosity determination, as outlined in the disclosure. Once progeny plants have been genotyped, and/or their zygosity determined, the skilled artisan may select those progeny plants that have a desired genetic composition. Such selected progeny plants may be used in further crosses, selfing, or cultivation. Methods of introgression of a fl2 mutation that are directed according to methods of the disclosure reduce or eliminate the cultivation and/or reproduction of plants that do not have a desired genetic composition, and thereby provide desirable reliability and predictability (through expected Mendelian patterns of inheritance).

The following Examples are provided to illustrate certain particular features and/or aspects. These Examples should not be construed to limit the disclosure to the particular features or aspects described.

EXAMPLES

Example 1

Cloning of the 22 kDa α-Zein Gene from DAS Germplasms

Select maize plant lines J15 and Oh-43 were requested from the maize genetic stock center and propagated by DAS plant breeders. Corn plants were derived from the J15 line and are homozygous for the floury2 trait. Likewise, additional corn plants were derived from the Oh-43 line and contain the floury2 trait. In addition, another group of corn plants lacking the floury phenotype (wild type) were used to develop the assay.

DNA Isolation

For DNA extraction, embryos dissected from seeds or fresh leaf punches were ground to a fine powder using a Genogrinder 2000™ and extracted with a standard MagAttract 96 DNA Plant Core Kit™ (Qiagen, Valencia, Calif.) using the customized BioCel Robot System™ from Agilent Technologies (Santa Clara, Calif.). Prior to PCR, DNA samples were quantified with the Quant-iT™ PicoGreen® Quantification Kit (Invitrogen, Carlsbad, Calif.) using the manufacturer's instructions.

PCR amplification and sequencing of 27-kDa α-zein

The maize B73 inbred genomic sequence of 22-kDa α-zein, containing approximately 1.7 kb with one single exon, was retrieved from NCBI (AC229981.2). Primers were designed based on the B73 sequence Zein_68F (SEQ ID NO:1 5'-GAGATCATGCATGTCATTCCA-3') Zein_68R (SEQ ID NO:2 5'-TTGGTGTTGTTAAGTTCA-CATGC-3') and PCR was performed in ABI GeneAmp® PCR System 9700 (Applied Biosystems, Foster City, Calif.) in reactions containing 2.5 units of TaKaRa LA Taq™ (Takara Bio Inc., Shiga, Japan), 400 nM of dNTP, 200 nM of forward and reverse primer and 30 ng of genomic DNA. The following PCR program was used: PCR started with 2 minutes of denaturing at 94° C. as recommended, followed by 30 cycles of 94° C. for 45 seconds, 55° C. for 45 seconds and 72° C. for 2 minutes. PCR products were visualized on a 2% E-Gel™ and then extracted using the Purelink™ Quick Gel Extraction kit (Invitrogen, Carlsbad, Calif.). Purified PCR products were then cloned into the pCR4-TOPO Vector™ (Invitrogen, Carlsbad, Calif.) per manufacturer's instruction. Selected colonies were grown overnight in 1× freezer media containing 2.5% LB (10 g tryptone, 10 g NaCl, and 5 g yeast extract for 1L LB media), 36 mM $K_2HPO_4$, 13 mM $KH_2PO_4$, 1.7 mM sodium citrate, 6.8 mM $(NH_4)_2SO_4$, 4.4% glycerol, 0.4 mM $MgSO_4$ $7H_2O$ and 12.5 µg/ml chloramphenicol (added immediately before use) with 50 µg/ml Kanamycin and outsourced to an external sequencing provider (Houston, Tex.) for sequencing with primers designed to bind to the T7 and T3 promoters (which flank the pCR4-TOPO™ vector insertion site) as well as oligos Zein513F (SEQ ID NO:3 5' AATCCTTGGCACATCTAA 3'), Zein-23R (SEQ ID NO:4 5' TAGGTGGCTCAGT-GATGGCAGAA 3') and Zein-385_R (SEQ ID NO:5 5' CTAAAAGATGGCACCTCCAA 3') within the 22-kDa α-zein gene. Sequences were analyzed using the Sequencher 4.8™ sequence alignment computer program.

KASPar® assay design and cycling conditions

The KBiosciences Competitive Allele Specific PCR® (KASPar®) assays based on SNPs or insertion and deletions (In/Dels) were designed (KBiosciences, Hoddesdon, Hertfordshire, UK). KASPar® reactions were set up according to Table 1 and Table 2. PCR cycles started at 94° C. for 15 minutes; then for 20 cycles with 10 seconds of denaturing at 94° C. and 5 seconds of annealing at 57° C.; then 10 seconds of extension at 72° C.; followed by 22 cycles with 10 seconds of denature at 94° C. and 20 seconds of annealing at 57° C.; then 40 seconds of extension at 72° C. ABI GeneAmp® PCR System 9700 (Applied Biosystems, Foster City, Calif.) was used for amplification. PCR products were measured by PheraStar Spectrofluorometer™ (BMG LABTECH Inc., Cary, N.C.) with excitation wavelength at 485 nm and emission wavelength at 520 nm for fluorescent signal of FAM and 520 nm and 560 nm for CAL.

TABLE 1

Recipe for assay mix set up.

|  | Concentration in Assay Mix (µM) | Volume in Assay Mix (µl) |
|---|---|---|
| Allele Specific Primer 1 (A1, 100 µM) | 12 | 12 |
| Allele Specific Primer 2 (A2, 100 µM) | 12 | 12 |
| Common (reverse) Primer (C1, 100 µM) | 30 | 30 |
| H₂0/TrisHCl (10 mM, pH 8.3) | — | 46 |
| TOTAL |  | 100 |

TABLE 2

Recipe for KASPar ® reaction in a 5 µl final volume.

| Component | volume (µl) |
|---|---|
| DNA (5 ng/µl): | 1 |
| 2X Reaction Mix: | 2.5 |
| Assay Mix: | 0.07 |
| *MgCl₂ (50 mM): | 0.04 |
| H₂O: | 1.39 |
| TOTAL: | 5 |

The 1.7 kb 22-kDa α-zein genomic fragments were successfully PCR-cloned from two floury lines and a wild type corn line. Sequences were aligned with B73 (NCBI accession AC229981.2) and a public fl2 allele (L34340, floury 2 mutant from W64fl2). A total of 72 SNPs and 7 insertion/deletion (InDels) were identified (FIG. 1) with 24 variations within the exon region. The substitution from alanine to valine at the −1 signal peptide, the cause of the floury appearance, is present in both fl2 corn line 2 and fl2 corn line 3 (FIG. 2), which originated from J15 and Oh-43, respectively.

Neither corn line contained the histidine insertion between the $164^{th}$ and $165^{th}$ amino acid or the alanine to threonine substitution at the $173^{rd}$ amino acid, the other two mutations reported to also be responsible for the floury2 phenotype. Efforts were focused on gene-specific assays to detect mutations from J15 and Oh43 that correlated with the floury2 phenotype. Comparison of fl2 corn line 2 with fl2 corn line 3 at the protein level revealed one change from histidine (H) to glutamine (Q) at amino acid position 159 (FIG. 2). Since there was no phenotypic variation reported between these two sources of floury2 mutations, no further characterization was conducted on this mutation.

Example 2

Gene-Specific Molecular Assay for Fl2

The alanine to valine substitution at the −1 position of the signal peptide is sufficient in creating the 24 kDa unprocessed α-zein and the floury2 phenotype. To develop gene-specific molecular assays for fl2, a KASPar® assay was designed based on this single nucleotide polymorphism from C to T. It was tested with a diverse panel of 23 maize inbred lines, including six lines of floury2 samples. The assay was effective at distinguishing the floury2 lines from the rest of the inbreds based on copy number variations of the mutant allele, which contains the SNP basepair C. However, wild type alleles with basepair T amplified from all samples with equal intensity, indicating the assay cannot be used for gene-specific detection (FIG. 3). This appeared to be mainly due to the high homology of 22-kDa α-zein with other zein family members. The α-zein family contains 75 members with more than 75% amino acid identity.

Four additional substitutions and two Ins/Dels with amino acid changes in the single exon of the 22-kDa α-zein gene (Table 3) were tested as candidates using the KASPar® molecular assay described. Most of the trials demonstrated the same cluster pattern as shown in FIG. 3 tested with 23 inbred maize lines. Although these assays could detect copy number variations, they were not sufficiently robust for large-scale zygosity analysis, where a clear separation between fl2 allele and the wild type allele is crucial.

Figure 4:
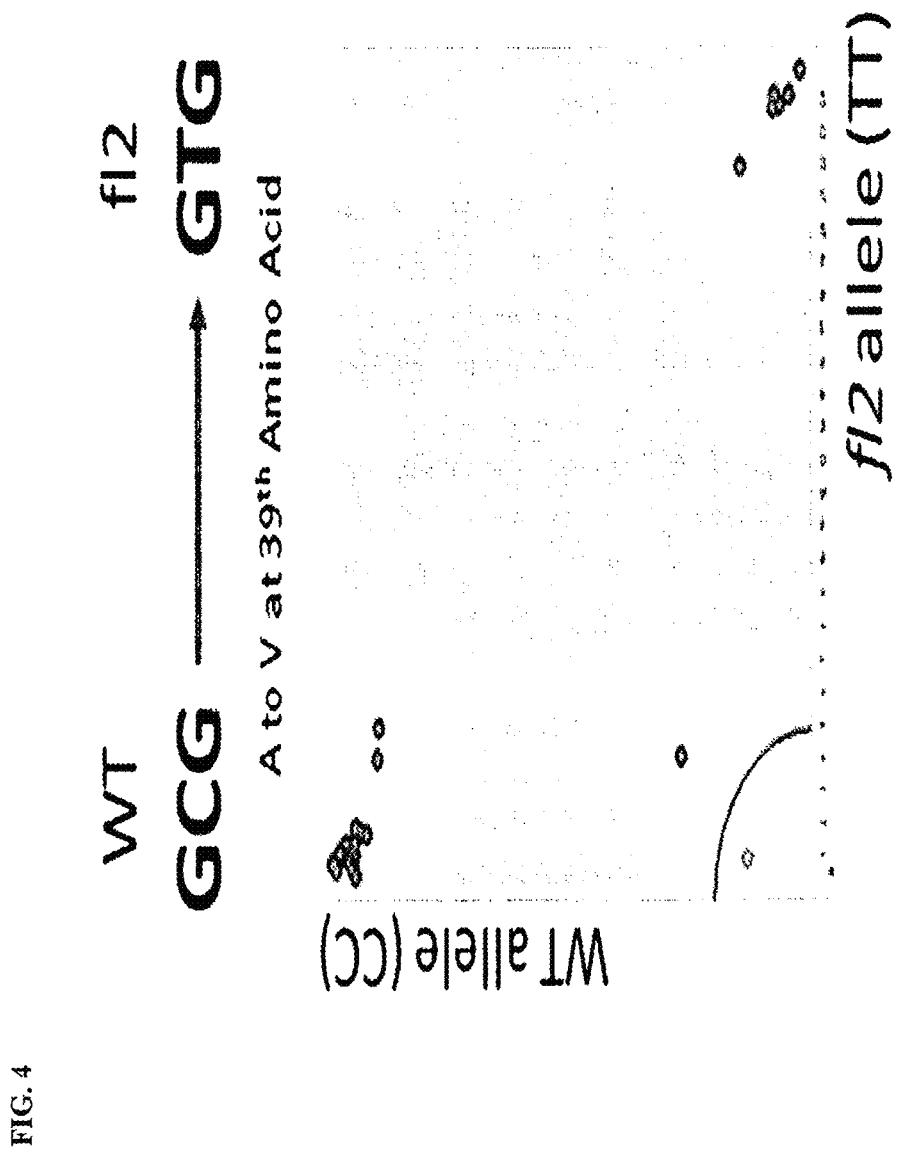
FIG. 4 shows the KLIMS Data analysis of 23 maize inbred lines genotyped with KASPar® assay based on the alanine to valine substitution at the $39^{th}$ amino acid (FAM signal for mutant allele as x-axis and CAL signal for wild type allele as y-axis).
Figure 5:
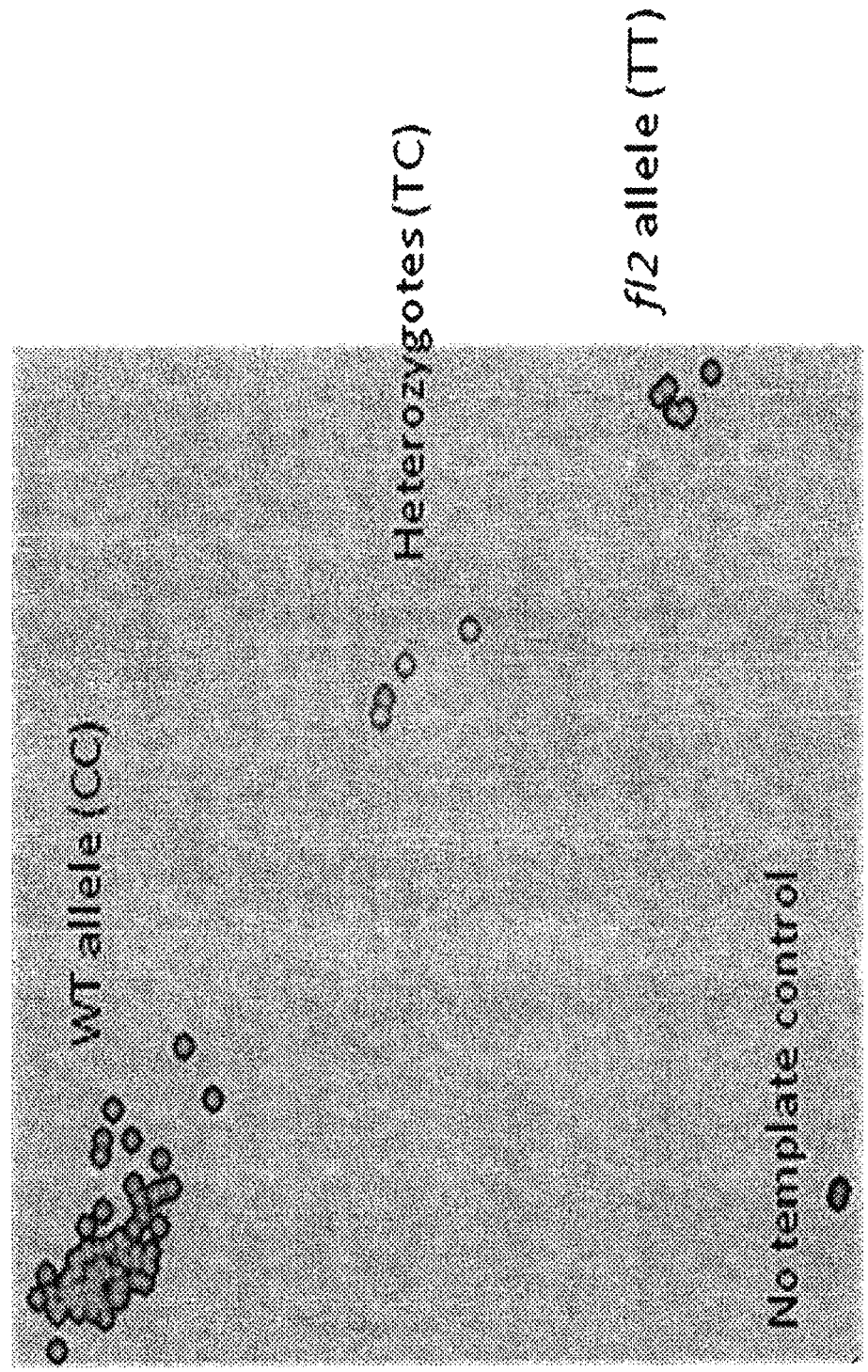
FIG. 5 shows a confirmation test with maize inbred lines genotyped with KASPar® assay based on the alanine to valine substitution at the 39$^{th}$ amino acid (FAM signal for mutant allele as x-axis and CAL signal for wild type allele as y-axis).

One KASPar® assay, however, based on the second alanine to valine substitution at the $39^{th}$ amino acid, produced distinct clusters between floury2 and wild type samples, with the FAM signal indicating the fl2 gene (FIG. 4). This assay is described in Table 3 as Assay Number 3. To confirm the specificity of the assay, an additional 82 non-floury maize inbred lines were then tested. All 82 wild type lines tested negative for the targeted fl2 allele, strongly indicating that the assay is highly selective for the floury2 gene. The assay was then named fl2_zygo.

TABLE 3

KASPar ® assays designed based on the variations within the exon of 22 kDa α-zein gene.

| Based on 1687 bp Nucleotide Sequence Alignment | | Based on 243 Amino Acid Sequence Alignment | | KASPar ® assay | | |
|---|---|---|---|---|---|---|
| Assay number | Position | mutation | Position | mutation | Oligos | SEQ ID NO: | Oligo sequences |
| 1 | 378 | C to T | −1 | Alanine to Valine | A1-1 | 19 | GAAGGTGACCAAGTTCATGCTCC CTTTTAGTGAGCGCAACAAATGT |
| | | | | | A2-1 | 20 | GAAGGTCGGAGTCAACGGATTCC TTTTAGTGAGCGCAACAAATGC |
| | | | | | C1-1 | 21 | GGAGCAAGTGAGCACTGTGGAAT AA |
| 2 | 417 | G to T | 13 | Serine to Isoleucine | A1-2 | 22 | GAAGGTGACCAAGTTCATGCTCA CTTGCTCCTAGTGCCAT |
| | | | | | A2-2 | 23 | GAAGGTCGGAGTCAACGGATTCT CACTTGCTCCTAGTGCCAG |

TABLE 3-continued

KASPar ® assays designed based on the variations within the exon of 22 kDa α-zein gene.

| Assay number | Based on 1687 bp Nucleotide Sequence Alignment | | Based on 243 Amino Acid Sequence Alignment | | KASPar ® assay | | |
|---|---|---|---|---|---|---|---|
| | Position | mutation | Position | mutation | Oligos | SEQ ID NO: | Oligo sequences |
| | | | | | C1-2 | 24 | AACTGGTGGGAGGAACTGTGGAATA |
| 3 | 495 | C to T | 39 | Alanine to Valine | A1 | 6 | GAAGGTGACCAAGTTCATGCTGCAAGCCTATAGGCTACAACTAGT |
| | | | | | A2 | 7 | GAAGGTCGGAGTCAACGGATTCAAGCCTATAGGCTACAACTAGC |
| | | | | | C1 | 8 | TGTTGCAATTGGGCAATTGGTTGTTGTAA |
| 4 | 638 | A to G | 88 | Threonine to Alanine | A1-3 | 25 | GAAGGTGACCAAGTTCATGCTCAGCTGCTGTTGCAAGTAGGC |
| | | | | | A2-3 | 26 | GAAGGTCGGAGTCAACGGATTGCAGCTGCTGTTGCAAGTAGGT |
| | | | | | C1-3 | 27 | TGAGCCACCTAGCCGTGGTGAA |
| 5 | 870 | TCA insertion | 164 | Histidine insertion | A1-4 | 28 | GAAGGTGACCAAGTTCATGCTATTGTACCAGCTCTGACTCAT |
| | | | | | A2-4 | 29 | GAAGGTCGGAGTCAACGGATTATTGTACCAGCTCTGACTCAG |
| | | | | | C1-4 | 30 | CAATTGGTTGAATGGAAGCA |
| 6 | 899 | G to A | 173 | Alanine to Threonine | A1-5 | 31 | GAAGGTGACCAAGTTCATGCTAATGGAAGCAACTGTTGTAAGTAGGT |
| | | | | | A2-5 | 32 | GAAGGTCGGAGTCAACGGATTATGGAAGCAACTGTTGTAAGTAGGC |
| | | | | | C1-5 | 33 | CGTACCTACAACAACAGTTGCTGCAA |
| 7 | 1036 | CAA deletion | 219 | Glutamine deletion | A1-6 | 34 | GAAGGTGACCAAGTTCATGCTGGTTGTATGGCAGCAATTGTTGC |
| | | | | | A2-6 | 35 | GAAGGTCGGAGTCAACGGATTCTGGTTGTATGGCAGCAATTGTTGT |
| | | | | | C1-6 | 36 | CAGTGGCTAACCCATTGGTCGCT |

Example 3

Assay Validation with Segregating Populations

Validation with segregating populations

Figure 6:
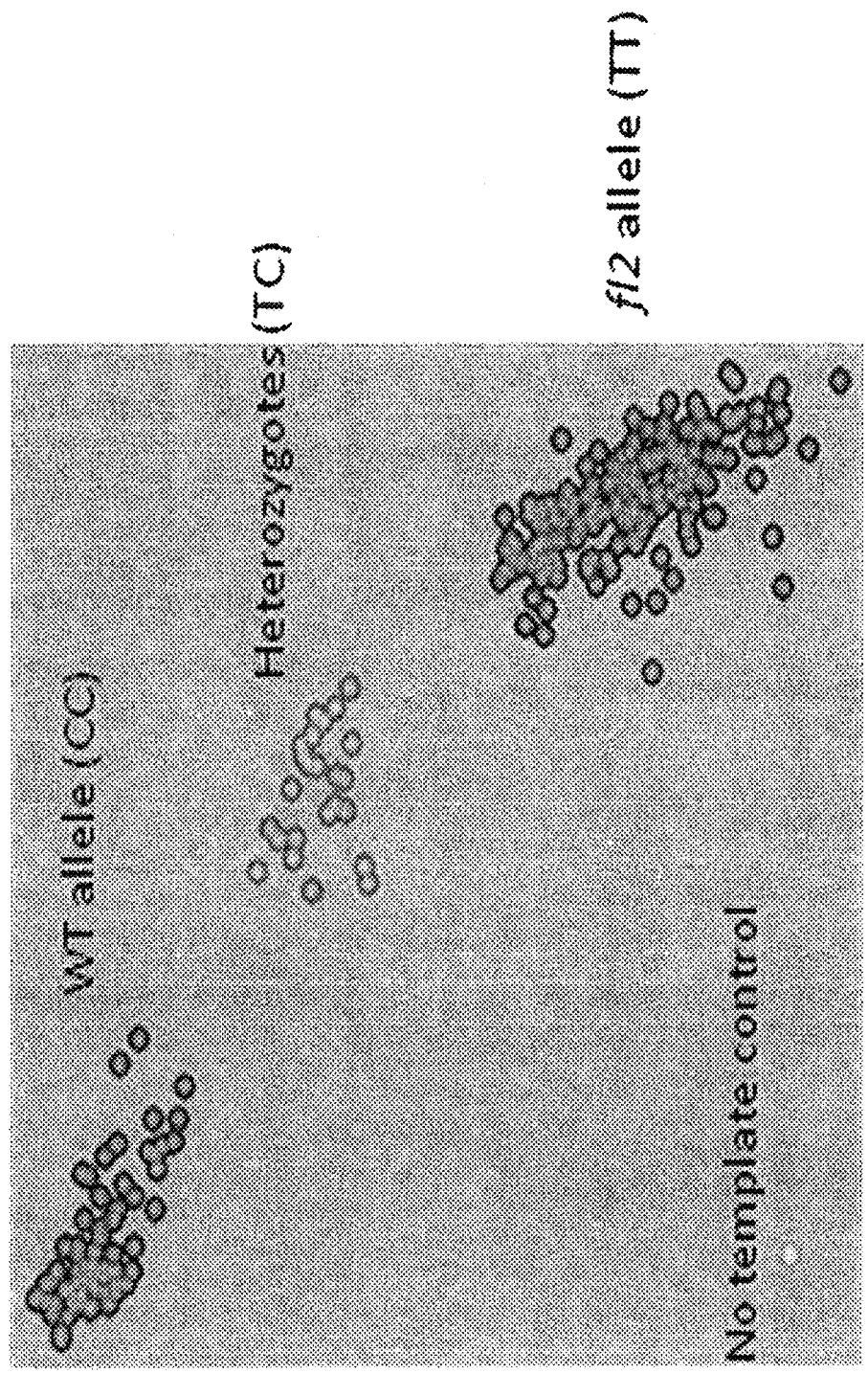
FIG. 6 shows a validation test with segregating populations genotyped with KASPar® assay (fl2_zygo) based on the alanine to valine substitution at the 39$^{th}$ amino acid (FAM signal for mutant allele as x-axis and CALs signal for wild type allele as y-axis).

The fl2_zygo gene-specific assay was validated using segregating samples from two genetic backgrounds. Each pool contained 25 samples. Ten seeds from each sample were dissected and DNA was extracted from embryos, with a total of 500 seeds (50 ears with 10 seeds per ear), and tested with fl2_zygo (FIG. 6). Samples with discrepancies were further evaluated with field experiments: ten seeds from each sample were planted in Arlington, Ill. Fresh leaf punches were harvested for DNA extraction and genotype testing. Plants were then self pollinated and the ears harvested. Phenotype data was collected by placing the kernels on a light box and scored based on a vitreousness scale: translucent-wildtype; partial opaque-heterozygotes and complete opaque-homozygotes.

The assay clearly distinguished among the homozygous, heterozygous and wild type genotypes. For homozygous floury2 as well as wild type ears, 97% had matching genotype and phenotype data, with more than half of the heterozygous ears (15 out of 26) showing discrepancies between genotype and phenotype results.

Validating the zygosity assay

With the ambiguity of the light box method, one would expect low accuracy when the phenotype relies on a small number of seeds. An ideal zygosity assay would, however, require a perfect match.

To further validate the specificity of the fl2_zygo assay, ten seeds from each ear with discrepancies were planted in Arlington; IL. DNA was extracted from leaf punches collected from 2 month old plants and genotyped with fl2_zygo. The plants were then self pollinated and seeds were harvested. The seeds were subjected to light box phenotyping after drying.

Comparison of the visual scoring with the genotype data from the fl2_zygo assay revealed a 95% match (145 out of 152), with the remaining seven ears all segregating with questionable phenotypes. These were either originated from Iodent lines with bronze discoloration, or had round, bulky shapes, and thus extremely difficult to score with a light box. If the phenotype was correct, there could be gene(s) in addition to the 22-kDa α-zein contributing to the floury2 trait, since all seven ears tested as wild type genetically. Using marker assisted selection, null plants were excluded from advancement. The alanine to valine substitution in the 22-kDa α-zein is sufficient to cause the floury2 mutation. Extended use of the gene-specific assay fl2_zygo should select against other mutations associated with the floury2 phenotype, given the high specificity of the assay for the 39 amino acid associated mutation. All fl2 donor lines currently in conversion contained the mutated 22-kDa α-zein and tested positive for the fl2 allele using fl2_zygo (data not shown).

Genotype and zygosity determinations from this fl2 gene-specific molecular matched very closely with phenotypic data collected from the field. This assay provides an easy, rapid, and accurate way to characterize the fl2 zygosity status using a high-throughput, molecular-based assay system.

Example 4

Introgression of the Floury2 (Fl2) Trait into Plant Lines

Introgression of fl2

Mutation fl2_zygo can be used as a robust assay for fl2 introgression. The zygosity of a corn plant with respect to the fl2 mutation may be determined as described in Examples 1-2. A selected corn plant determined homozygous for the fl2 mutation may be crossed through conventional plant breeding with a corn plant known to be homozygous for a desired trait, such as BMR or COMT. $F_1$ progeny may then be selfed to produce $F_2$ progeny. Samples of genomic DNA of the $F_2$ progeny may be prepared and the zygosity of the $F_2$ progeny plants determined as described, supra. $F_2$ progeny plants that are homozygous for the fl2 mutation may then be selected. The selected progeny are then assayed for high lysine content, reduced cell wall lignin content and/or increased digestibility, and those progeny that exhibit desirable traits may be further reproduced by crossing and selfing, with the resulting progeny are cultivated.

While the present invention has been described herein with respect to certain preferred embodiments, those of ordinary skill in the art will recognize and appreciate that it is not so limited. Rather, many additions, deletions, and modifications to the preferred embodiments may be made without departing from the scope of the invention as hereinafter claimed. In addition, features from one embodiment may be combined with features of another embodiment while still being encompassed within the scope of the invention as contemplated by the inventors.

---

What is claimed is:

1. A method for determining the zygosity and/or presence/absence of an allele in a corn plant tissue, the method comprising:
   obtaining a sample of isolated genomic DNA from the corn plant tissue;
   contacting the isolated genomic DNA with at least one nucleic acid molecule comprising a nucleotide sequence capable of hybridizing to SEQ ID NO:9 under high stringency conditions and at least one nucleic acid molecule capable of hybridizing to SEQ ID NO:10 under high stringency conditions; and
   determining the zygosity of fl2 mutation in the isolated genomic DNA,
   wherein the fl2 mutation comprises a (C/T) single nucleotide polymorphism (SNP) at nucleotide position 495 of SEQ ID NO:9 or SEQ ID NO:10,
   specifically detecting the (C/T) SNP at nucleotide position 495 of SEQ ID NO:9 or SEQ ID NO:10 via a KASPar® PCR assay,
   generating zygosity genotype data of the fl2 mutation, and
   comparing the zygosity genotype data with phenotype data collected from the field,
   wherein the accuracy rate of homozygous genotype data with the phenotype data collected from the field is at least about 97% and the accuracy rate of heterozygous genotype data with the phenotype data collected from the field is at least about 42%.

2. The method of claim 1, further comprising:
   contacting the isolated genomic DNA with two nucleic acid molecules each comprising a nucleotide sequence capable of hybridizing to SEQ ID NO:9 under high stringency conditions, and two nucleic acid molecules capable of hybridizing to SEQ ID NO:10 under high stringency conditions;
   amplifying the nucleotide sequence of the isolated genomic DNA between nucleotide sequences of the isolated genomic DNA that hybridize to the two nucleic acid molecules each comprising a nucleotide sequence capable of hybridizing to SEQ ID NO:9 under high stringency conditions;
   amplifying the nucleotide sequence of the isolated genomic DNA between nucleotide sequences of the isolated genomic DNA that hybridize to the two nucleic acid molecules each comprising a nucleotide sequence capable of hybridizing to SEQ ID NO:10 under high stringency conditions;
   including in the amplifying reaction at least one nucleic acid molecule comprising a nucleotide sequence capable of hybridizing to SEQ ID NO:9 under high stringency conditions that is labeled with a first reporter, and at least one nucleic acid molecule capable of hybridizing to SEQ ID NO:10 under high stringency conditions that is labeled with a second reporter; and
   detecting the levels of the first and second reporter.

3. The method of claim 2, wherein the first reporter and the second reporter are fluorescent dyes with distinguishable excitation/emission spectra.

4. The method of claim 3, wherein the first reporter is FAM, and the second reporter is VIC.

5. The method of claim 1, wherein the at least one nucleic acid molecule comprising a nucleotide sequence capable of hybridizing to SEQ ID NO:9 is between 10 and 35 nucleotides in length.

6. The method of claim 5, wherein the at least one nucleic acid molecule comprising a nucleotide sequence capable of hybridizing to SEQ ID NO:9 is between 15 and 30 nucleotides in length.

7. The method of claim 5, wherein one of the at least one nucleic acid molecules comprising a nucleotide sequence capable of hybridizing to SEQ ID NO:9 is at least 95% identical to between 10 and 35 contiguous nucleotides of SEQ ID NO:9.

8. The method of claim 7, wherein the at least one nucleic acid molecule comprising a nucleotide sequence capable of hybridizing to SEQ ID NO:9 is selected from the group consisting of SEQ ID NO:6, SEQ ID NO:7, and SEQ ID NO:8.

9. The method of claim 1, wherein at least one nucleic acid molecule comprising a nucleotide sequence capable of hybridizing to SEQ ID NO:9 under high stringency conditions is labeled with a fluorescent dye, and at least one nucleic acid molecule capable of hybridizing to SEQ ID NO:10 under high stringency conditions is labeled with a second fluorescent dye with a distinguishable excitation/emission spectra.

10. The method of claim 9, wherein at least one nucleic acid molecule comprising a nucleotide sequence capable of hybridizing to SEQ ID NO:9 under high stringency conditions is labeled with FAM, and at least one nucleic acid molecule capable of hybridizing to SEQ ID NO:10 under high stringency conditions is labeled with VIC.

11. The method of claim 2, wherein amplifying the nucleotide sequence comprises amplifying in a high throughput PCR reaction.

12. A method for reliably and predictably introgressing a trait for high lysine content into plant germplasm, said method comprising:
   crossing a plant having a mutation in the fl2 gene with another plant;
   obtaining a sample of isolated genomic DNA from a progeny plant produced by the cross;
   contacting the isolated nucleic acid with at least one nucleic acid molecule having a nucleotide sequence capable of hybridizing to SEQ ID NO:10 under high stringency conditions;

selecting progeny from the cross that comprise a mutation in the fl2 gene, wherein the mutation in the fl2 gene is associated with a trait for high lysine content and comprises a (C/T) single nucleotide polymorphism (SNP) at nucleotide position 495 of SEQ ID NO:10, reproducing a plant from which a sample was obtained that binds the at least one nucleic acid molecules with high stringency, and producing a genetically engineered plant wherein the trait for high lysine content has been introgressed into the germplasm of the genetically engineered plant via a KASPar® PCR assay, and detecting the allele-specific genotype of the fl2 mutation comprised by the genetically engineered plant, and comparing allele-specific genotype data to high lysine phenotype data collected from the field, wherein the accuracy rate of homozygous allele-specific genotype data with the phenotype data collected from the field is at least about 97% and the accuracy rate of heterozygous allele-specific genotype data with the phenotype data collected from the field is at least about 42%.

13. The method of claim 12, wherein the at least one nucleic acid molecule comprising a nucleotide sequence capable of hybridizing to SEQ ID NO:10 is between 10 and 35 nucleotides in length.

14. The method of claim 12, wherein the at least one nucleic acid molecule comprising a nucleotide sequence capable of hybridizing to SEQ ID NO:10 is between 15 and 30 nucleotides in length.

15. The method of claim 12, wherein the at least one nucleic acid molecule capable of hybridizing to SEQ ID NO:10 under high stringency conditions is labeled with a fluorescent dye with a distinguishable excitation/emission spectra.

16. The method of claim 15, wherein the fluorescent dye with a distinguishable excitation/emission spectra is VIC.

17. The method of claim 15, wherein the fluorescent dye with a distinguishable excitation/emission spectra is FAM.

* * * * *

SEQUENCE LISTING

```
<160> NUMBER OF SEQ ID NOS: 36

<210> SEQ ID NO 1
<211> LENGTH: 21
<212> TYPE: DNA
<213> ORGANISM: Artificial Sequence
<220> FEATURE:
<223> OTHER INFORMATION: forward primer sequence Zein_68F

<400> SEQUENCE: 1
gagatcatgc atgtcattcc a                                              21

<210> SEQ ID NO 2
<211> LENGTH: 23
<212> TYPE: DNA
<213> ORGANISM: Artificial Sequence
<220> FEATURE:
<223> OTHER INFORMATION: reverse primer sequence Zein_68R

<400> SEQUENCE: 2
ttggtgttgt taagttcaca tgc                                            23

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide sequence Zein_513F

<400> SEQUENCE: 3
aatccttggc acatctaa                                                  18

<210> SEQ ID NO 4
<211> LENGTH: 23
<212> TYPE: DNA
<213> ORGANISM: Artificial Sequence
<220> FEATURE:
<223> OTHER INFORMATION: Oligonucleotide sequence Zein-23R

<400> SEQUENCE: 4
taggtggctc agtgatggca gaa                                            23
```

```
<210> SEQ ID NO 5
<211> LENGTH: 20
<212> TYPE: DNA
<213> ORGANISM: Artificial Sequence
<220> FEATURE:
<223> OTHER INFORMATION: Oligonucleotide sequence Zein-385_R

<400> SEQUENCE: 5
ctaaaagatg gcacctccaa                                                    20

<210> SEQ ID NO 6
<211> LENGTH: 45
<212> TYPE: DNA
<213> ORGANISM: Artificial Sequence
<220> FEATURE:
<223> OTHER INFORMATION: Primer Sequence A1

<400> SEQUENCE: 6
gaaggtgacc aagttcatgc tgcaagccta taggctacaa ctagt                        45

<210> SEQ ID NO 7
<211> LENGTH: 44
<212> TYPE: DNA
<213> ORGANISM: Artificial Sequence
<220> FEATURE:
<223> OTHER INFORMATION: Primer sequence A2

<400> SEQUENCE: 7
gaaggtcgga gtcaacggat tcaagcctat aggctacaac tagc                         44

<210> SEQ ID NO 8
<211> LENGTH: 29
<212> TYPE: DNA
<213> ORGANISM: Artificial Sequence
<220> FEATURE:
<223> OTHER INFORMATION: Primer sequence C1

<400> SEQUENCE: 8
tgttgcaatt gggcaattgg ttgttgtaa                                          29

<210> SEQ ID NO 9
<211> LENGTH: 1678
<212> TYPE: DNA
<213> ORGANISM: Zea mays

<400> SEQUENCE: 9
gagatcatgc atgtcattcc acataaatga aagaattcc tatataaaaa tgacatgttt         60
tgttgtaggt agtggaaatt atctttccag caaagaccat ataatccgat aaagctgata      120
actaaatgtc aaaatcgagt aagtgccata tcatctatat cttatctgtt gtttggaaaa      180
agacaaaatc caaaaaaaat atatgagatc tcacatgtat aaatagctcc caaatcagta      240
gttaatacat ctcccataat attttcagca ttcaaaaaca caccaagcga agcgcactag      300
caacgaccta acaccaatgg ctaccaagat attagccctc cttgcgcttc ttgcccttt       360 agtgagcgca acaaatgcgt tcattattcc acagtgctca cttgctccta gtgccagtat      420
tccacagttc ctcccaccag ttacttcaat gggcttcgaa catccagccg tgcaagccta      480
caggctacaa ctagcgcttg cggcgagcgc cttacaacaa ccaattgccc aattgcaaca      540
acaatccttg gcacatctaa ccctacaaac cattgcaacg caacaacaac aacaacagtt      600
tctgccatca ctgagccacc tagccgtggt gaaccctgtc acctacttgc aacagcagct      660
gcttgcatcc aacccacttg ctctggcgaa cgtagctgca taccagcaac aacaacagct      720
```

| | |
|---|---|
| gcaacagttt atgccagtgc tcagtcaact agccatggtg aaccctgccg tctacctaca | 780 |
| actactttca tctagcccgc tcgcggtggg caatgcacct acgtacctac aacaacagtt | 840 |
| gctgcaacaa attgtaccag ctctgactca gctagctgtg caaaccctg ctgcctactt | 900 |
| acaacagttg cttccattca accaactggc tgtgtcaaac tctgctgcgt acctacaaca | 960 |
| gcgacaacag ttacttaatc cattggcagt ggctaaccca ttggtcgcta ccttcctgca | 1020 |
| gcagcaacaa caattgctgc catacaacca gttctctttg atgaaccctg ccttgcagca | 1080 |
| acccatcgtt ggaggtgcca tcttttagat tacatatgag atgtactcga caatggtgcc | 1140 |
| ctcataccga catgtgtttc ctagaaataa tcaatatatt gattgagatt tatctcgata | 1200 |
| tatttctgaa ctatgttcat catataaata attgaaaaca tcaaatcata atttttaaact | 1260 |
| catgcttggt caatacatag ataatacaat attacttcat catcccaatg atgtcctagc | 1320 |
| ccaacctatt gaatgttaat gtttggttgt gtgagggtgt gtttataaca tagatgtgat | 1380 |
| tatttgcgct ttttgttgag tatatacata tatggtatgt tgatttgata tagtgatgga | 1440 |
| cacatgcttt ggccttggat attcaaatca cttgtacttg cacgaagcaa aacataatat | 1500 |
| aagtttagaa gtaaacttgt aactatgtcc aaacatgctc acacaaagtc ataccgcatt | 1560 |
| ataattttt ggtaaatatt caacacatgt attttttaca agaacccaaa ttttacagac | 1620 |
| aaatgcagca ttgtagacat gtagaattct ttgaagcatg tgaacttaac aacaccaa | 1678 |

<210> SEQ ID NO 10
<211> LENGTH: 1674
<212> TYPE: DNA
<213> ORGANISM: Zea mays

<400> SEQUENCE: 10

| | |
|---|---|
| gagatcatgc atgtcattcc acataaatga aaagaattcc tatataaaaa cgacatgttt | 60 |
| tgttgtaggt agtggaaact atcttttccag caaagaccat ataatccgat aaagctgata | 120 |
| actaaatgtc gaaatcgagt aggtgccata tcatctatat cttatctgtt gtttggaaaa | 180 |
| agacaaaatc caaaaaaaat atatgagatc tcacctgtat aaatagctcc caaatcagta | 240 |
| gttaatacat ctcccataat attttcagca ttcagaaaca caccaagcga acgactagca | 300 |
| acgacctaac aacaatggct accaagatat tagccctcct tgcgcttctt gcccttttag | 360 |
| tgagcgcaac aaatgtgttc attattccac agtgctcact tgctcctagt gccattattc | 420 |
| cacagttcct cccaccagtt acttcaatgg gcttcgaaca tccagccgtg caagcctata | 480 |
| ggctacaact agtgcttgcg gcgagcgcct acaacaacc aattgcccaa ttgcaacaac | 540 |
| aatccttggc acatctaacc ctacaaacca tcgcaacgca acaacaacaa catttttctgc | 600 |
| catcactgag ccacctagca gtggtgaacc ctgtcgccta cttgcaacag cagctgcttg | 660 |
| catccaaccc acttgctctg gcgaacgtag ctacatacca gcaacaacaa cagctgcaac | 720 |
| agtttatgcc agcgctcagt caactagcca tggtgaaccc tgccgtctac ctacaactgc | 780 |
| tttcatctag cccgctcgct gtgggcaatg cacctacgta cctacaacaa cagttgctgc | 840 |
| aacagattgt accagctcta actcatcagc tagctatggc aaaccctgct acctacttac | 900 |
| aacagttgct tccattcaac caattggctg tgtcgaactc tgctgcgtac ctacaacagc | 960 |
| gacaacaatt acttaatcca ttggcagtgg ctaacccatt ggtcgctacc ttcctgcagc | 1020 |
| agcaacaatt gctgccatac aaccagttct ctttgatgaa ccctgccttg cagcaaccca | 1080 |
| tcgttggagg tgccatcttt tagattacat atgagatgta ctcgacaatg gtgccctcat | 1140 |
| accggcatgt gtttcctaga aataatcaat atattgattg agatttatct cgatatattt | 1200 |

```
ctgaactatg ttcatcatat aaataactga aaacatcaaa tcgtaatttt aaagctcatg    1260
cttggtcaat acatagataa tacaatatta cttcatcatc ccaatgatgt cctagcacaa    1320
cctattgaat gttaatgttt ggttgtgtgg gggtgtgttt ataacataga tgtgattatt    1380
tgtgcttttt gttgagtata tacatatatg gtatgttgat ttgatatagt gatggacaca    1440
tgctttggcc ttggatattc aaatcacttg tacttgcacg aagcaaaaca taatataagt    1500
ttagaagtaa acttgtaact gtgtccaaac atgctcacac aaagtcatat cgcattatat    1560
ttttttggta aatattcaac acatgtattt tttacaagaa cccaaatttt acagacaaat    1620
gcagcattgt agacatgtag aattctttga agcatgtgaa cttaacaaca ccaa          1674
```

<210> SEQ ID NO 11
<211> LENGTH: 1687
<212> TYPE: DNA
<213> ORGANISM: Zea mays

<400> SEQUENCE: 11

```
gagatcatgc atgtcattcc acataaatga aagaattcc tatataaaaa cgacatgttt    60
tgttgtaggt agtggaaact atctttccag caaagaccat ataatccgat aaagctgata    120
actaaatgtc gaaatcgagt aggtgccata tcatctatat cttatctgtt gtttggaaaa    180
agacaaaatc caaaaaaat atatgagatc tcacttgtat aaatagctcc caatcagta     240 gttaatacat ctcccataat attttcagca ttcagaaaca caccaagcga agcgcactag    300
caacgaccta acaacaatgg ctaccaagat attagccctc cttgcgcttc ttgccctttt    360
agtgagcgca acaaatgtgt tcattattcc acagtgctca cttgctccta gtgccattat    420
tccacagttc ctcccaccag ttacttcaat gggcttcgaa catccagccg tgcaagccta    480
taggctacaa ctagtgcttg cggcgagcgc cttacaacaa ccaattgccc aattgcaaca    540
acaatccttg gcacatctaa ccctacaaac catcgcaacg caacagcaac aacagttcct    600
gccatcactg agccacctag ccgtggtgaa ccctgtcgcc tacttgcaac agcagctgct    660
tgcatccaac ccacttgctc tggcaaacgt agttgcaaac cagcaacaac aacagctgca    720
acagtttctg ccagcgctca gtcaactagc catggtgaac cctgccgcct acctacaaca    780
gcaacaactg ctttcatcta gcccgctcgc tgtggccaat gcacctacat acctgcaaca    840
acaattgttg caacagattg taccagctct aactcagcta gctgtggcaa accctgctgc    900
ctacttgcaa cagctgcttc cattcaacca actgactgtg tcgaactctg ctgcgtacct    960
acaacagcga caacagttac ttaatccatt ggcagtggct aacccattgg tcgctgcctt    1020
cctacagcag caacaattgc tgccatacaa ccagttctct ttgatgaacc ctgtcttgtc    1080
gaggcagcaa cccatcgttg gaggtgccat cttttagatt acatatgaga tgtactcgat    1140
aatggtgccc tcataccggc atgtgtttcc tagaaataat caatatattg attgagattt    1200
atctcgatat atttctgaac tatgttcatc atataaataa ttgaaaacat caaatcgtaa    1260
ttataaactc atgcttggtc aatacataga taatacaata ttacttcatc atcccaatga    1320
tgtcctagca caacctattg aatgttaatg tttggttgtg tgagggtgtg tttataacat    1380
agatgtgatt atttgcgctt tttgttgagt acatacatat atggtatgtt gatttgatat    1440
agtgatggac acatgctttg accatgaata ttcaaatcag ttgtatttgc acgaagcaaa    1500
acataatata agtttaggag tacacttata actgtgtcca aacatgctca cacaaattca    1560
taccacatta taatttttg gtaaatattc cacacatgta ttttttacaa gaacccaaat    1620
```

| tttacagaca aatgcagcat tgtagacatg tagaattctt tgaagcatgt gaacttaaca | 1680 |
| acaccaa | 1687 |

<210> SEQ ID NO 12
<211> LENGTH: 1687
<212> TYPE: DNA
<213> ORGANISM: Zea mays

<400> SEQUENCE: 12

| gagatcatgc atgtcattcc acataaatga aaagaattcc tatataaaaa cgacatgttt | 60 |
| tgttgtaggt agtggaaact atctttccag caaagaccat ataatccgat aaagctgata | 120 |
| actaaatgtc gaaatcgagt aggtgccata tcatctatat cttatctgtt gtttggaaaa | 180 |
| agacaaaatc caaaaaaaat atatgagatc tcacttgtat aaatagctcc caaatcagta | 240 |
| gttaatacat ctcccataat attttcagca ttcagaaaca caccaagcga agtgcactag | 300 |
| caacgaccta acaacaatgg ctaccaagat attagccctc cttgcgcttc ttgccctttt | 360 |
| agtgagcgca acaaatgtgt tcattattcc acagtgctca cttgctccta gtgccattat | 420 |
| tccacagttc ctcccaccag ttacttcaat gggcttcgaa catccagccg tgcaagccta | 480 |
| taggctacaa ctagtgcttg cggcgagcgc cttacaacaa ccaattgccc aattgcaaca | 540 |
| acaatccttg gcacatctaa ccctacaaac catcgcaacg caacaacaac aacagtttct | 600 |
| gccatcactg agccacctag ccgtggtgaa ccctgtcgcc tacttgcaac agcagctgct | 660 |
| tgcatccaac ccacttgctc tggcaaacgt agttgcaaac cagcaacaac aacagctgca | 720 |
| acagtttctg ccagcgctca gtcaactagc catggtgaac cctaccgcct acctacaaca | 780 |
| gcaacaactg ctttcatcta gcccgctcgc tgtggccaat gcacctacat acctgcaaca | 840 |
| acaattgttg caacatattg taccagctct gactcagcta gctgtggcaa accctgctgc | 900 |
| ctacttgcaa cagctgcttc cattcaacca actgactgtg tcgaactctg ctgcgtacct | 960 |
| acaacagcga caacagttac ttaatccact ggcagtggct aacccattgg tcgctgcctt | 1020 |
| cctacagcag caacaattgc tgccatacaa ccagttctct ttgatgaacc ctgtcttgtc | 1080 |
| gaggcagcaa cccatcgttg gaggtgccat cttttagatt acatatgaga tgtactcgat | 1140 |
| aatggcgccc tcataccggc atgtgttttc tagaaataat caatatattg attgagattt | 1200 |
| atctcgatat atttctgaac tatgttcatc atataaataa ttgaaaacat caaatcgtaa | 1260 |
| ttataaactc atccttggtc aatacataga taatacaata ttacttcatc atcccaatga | 1320 |
| tgtcctagcc caacctattg aatgttaatg tttggttgtg tgagggtgtg tttataacat | 1380 |
| agatgtgatt atttgcgctt tttgttgagt acatacatat atggtatgtt gatttgatat | 1440 |
| agtgatggac acatgctttg accatgaata ttcaaatcag ttgtacttgc acgaagcaaa | 1500 |
| gcataacata agtttaggag tagacttata actatgtcca aacatgctca cacaaattca | 1560 |
| taccacatta taattttttg gtaaatattc cacacatgta ttttttacaa gaacccaaat | 1620 |
| tttacagaca aatgcagcat tgtagacatg tagaattctt tgaagcatgt gaacttaaca | 1680 |
| acaccaa | 1687 |

<210> SEQ ID NO 13
<211> LENGTH: 1678
<212> TYPE: DNA
<213> ORGANISM: Zea mays

<400> SEQUENCE: 13

| gagatcatgc atgtcattcc acataaatga aaagaattcc tatataaaaa tgacatgttt | 60 |

```
tgttgtaggt agtggaaatt atctttccag caaagaccat ataatccgat aaagctgata    120
actaaatgtc aaaatcgagt aagtgccata tcatctatat cttatctgtt gtttggaaaa    180
agacaaaatc caaaaaaaat atatgagatc tcacatgtat aaatagctcc caaatcagta    240
gttaatacat ctcccataat attttcagca ttcaaaaaca caccaagcga agcgcactag    300
caacgaccta acaccaatgg ctaccaagat attagccctc cttgcgcttc ttgccctttt    360
agtgagcgca acaaatgcgt tcattattcc acagtgctca cttgctccta gtgccagtat    420
tccacagttc ctcccaccag ttacttcaat gggcttcgaa catccagccg tgcaagccta    480
caggctacaa ctagcgcttg cggcgagcgc cttacaacaa ccaattgccc aattgcaaca    540
acaatccttg gcacatctaa ccctacaaac cattgcaacg caacaacaac aacaacagtt    600
tctgccatca ctgagccacc tagccgtggt gaaccctgtc acctacttgc aacagcagct    660
gcttgcatcc aacccacttg ctctggcgaa cgtagctgca taccagcaac aacaacagct    720
gcaacagttt atgccagtgc tcagtcaact agccatggtg aaccctgccg tctacctaca    780
actactttca tctagcccgc tcgcggtggg caatgcacct acgtacctac aacaacagtt    840
gctgcaacaa attgtaccag ctctgactca gctagctgtg gcaaaccctg ctgcctactt    900
acaacagttg cttccattca accaactggc tgtgtcaaac tctgctgcgt acctacaaca    960
gcgacaacag ttacttaatc cattggcagt ggctaaccca ttggtcgcta ccttcctgca   1020
gcagcaacaa caattgctgc catacaacca gttctctttg atgaaccctg ccttgcagca   1080
acccatcgtt ggaggtgcca tcttttagat tacatatgag atgtactcga caatggtgcc   1140
ctcataccga catgtgtttc ctagaaataa tcaatatatt gattgagatt tatctcgata   1200
tatttctgaa ctatgttcat catataaata attgaaaaca tcaaatcata attttaaact   1260
catgcttggt caatacatag ataatacaat attacttcat catcccaatg atgtcctagc   1320
ccaacctatt gaatgttaat gtttggttgt gtgagggtgt gtttataaca tagatgtgat   1380
tatttgcgct ttttgttgag tacatacata tatggtatgt tgatttgata tagtgatgga   1440
cacatgcttt ggccttggat attcaaatca cttgtacttg cacgaagcaa acataaatat   1500
aagtttagaa gtaaacttgt aactatgtcc aaacatgctc acacaaagtc ataccgcatt   1560 ataattttt ggtaaatatt caacacatgt attttttaca agaacccaaa ttttacagac   1620
aaatgcagca ttgtagacat gtagaattct ttgaagcatg tgaacttaac aacaccaa    1678
```

<210> SEQ ID NO 14
<211> LENGTH: 263
<212> TYPE: PRT
<213> ORGANISM: Zea mays

<400> SEQUENCE: 14

```
Met Ala Thr Lys Ile Leu Ala Leu Leu Ala Leu Leu Ala Leu Leu Val
1               5                   10                  15

Ser Ala Thr Asn Ala Phe Ile Ile Pro Gln Cys Ser Leu Ala Pro Ser
            20                  25                  30

Ala Ser Ile Pro Gln Phe Leu Pro Pro Val Thr Ser Met Gly Phe Glu
        35                  40                  45

His Pro Ala Val Gln Ala Tyr Arg Leu Gln Leu Ala Leu Ala Ala Ser
    50                  55                  60

Ala Leu Gln Gln Pro Ile Ala Gln Leu Gln Gln Ser Leu Ala His
65                  70                  75                  80

Leu Thr Leu Gln Thr Ile Ala Thr Gln Gln Gln Gln Gln Gln Phe Leu
```

```
                    85                  90                  95
Pro Ser Leu Ser His Leu Ala Val Val Asn Pro Val Thr Tyr Leu Gln
            100                 105                 110
Gln Gln Leu Leu Ala Ser Asn Pro Leu Ala Leu Ala Asn Val Ala Ala
            115                 120                 125
Tyr Gln Gln Gln Gln Leu Gln Gln Phe Met Pro Val Leu Ser Gln
    130                 135                 140
Leu Ala Met Val Asn Pro Ala Val Tyr Leu Gln Leu Leu Ser Ser Ser
145                 150                 155                 160
Pro Leu Ala Val Gly Asn Ala Pro Thr Tyr Leu Gln Gln Gln Leu Leu
                165                 170                 175
Gln Gln Ile Val Pro Ala Leu Thr Gln Leu Ala Val Ala Asn Pro Ala
            180                 185                 190
Ala Tyr Leu Gln Gln Leu Leu Pro Phe Asn Gln Leu Ala Val Ser Asn
            195                 200                 205
Ser Ala Ala Tyr Leu Gln Gln Arg Gln Gln Leu Leu Asn Pro Leu Ala
    210                 215                 220
Val Ala Asn Pro Leu Val Ala Thr Phe Leu Gln Gln Gln Gln Gln Leu
225                 230                 235                 240
Leu Pro Tyr Asn Gln Phe Ser Leu Met Asn Pro Ala Leu Gln Gln Pro
                245                 250                 255
Ile Val Gly Gly Ala Ile Phe
            260

<210> SEQ ID NO 15
<211> LENGTH: 262
<212> TYPE: PRT
<213> ORGANISM: Zea mays

<400> SEQUENCE: 15

Met Ala Thr Lys Ile Leu Ala Leu Leu Ala Leu Leu Ala Leu Leu Val
1               5                   10                  15
Ser Ala Thr Asn Val Phe Ile Ile Pro Gln Cys Ser Leu Ala Pro Ser
                20                  25                  30
Ala Ile Ile Pro Gln Phe Leu Pro Pro Val Thr Ser Met Gly Phe Glu
            35                  40                  45
His Pro Ala Val Gln Ala Tyr Arg Leu Gln Leu Val Leu Ala Ala Ser
    50                  55                  60
Ala Leu Gln Gln Pro Ile Ala Gln Leu Gln Gln Gln Ser Leu Ala His
65                  70                  75                  80
Leu Thr Leu Gln Thr Ile Ala Thr Gln Gln Gln Gln His Phe Leu Pro
                85                  90                  95
Ser Leu Ser His Leu Ala Val Val Asn Pro Val Ala Tyr Leu Gln Gln
            100                 105                 110
Gln Leu Leu Ala Ser Asn Pro Leu Ala Leu Ala Asn Val Ala Thr Tyr
            115                 120                 125
Gln Gln Gln Gln Gln Leu Gln Gln Phe Met Pro Ala Leu Ser Gln Leu
    130                 135                 140
Ala Met Val Asn Pro Ala Val Tyr Leu Gln Leu Leu Ser Ser Ser Pro
145                 150                 155                 160
Leu Ala Val Gly Asn Ala Pro Thr Tyr Leu Gln Gln Gln Leu Leu Gln
                165                 170                 175
Gln Ile Val Pro Ala Leu Thr His Gln Leu Ala Met Ala Asn Pro Ala
            180                 185                 190
```

```
Thr Tyr Leu Gln Gln Leu Leu Pro Phe Asn Gln Leu Ala Val Ser Asn
        195                 200                 205

Ser Ala Ala Tyr Leu Gln Gln Arg Gln Gln Leu Leu Asn Pro Leu Ala
    210                 215                 220

Val Ala Asn Pro Leu Val Ala Thr Phe Leu Gln Gln Gln Gln Leu Leu
225                 230                 235                 240

Pro Tyr Asn Gln Phe Ser Leu Met Asn Pro Ala Leu Gln Gln Pro Ile
                245                 250                 255

Val Gly Gly Ala Ile Phe
            260

<210> SEQ ID NO 16
<211> LENGTH: 266
<212> TYPE: PRT
<213> ORGANISM: Zea mays

<400> SEQUENCE: 16

Met Ala Thr Lys Ile Leu Ala Leu Leu Ala Leu Leu Ala Leu Leu Val
1               5                   10                  15

Ser Ala Thr Asn Val Phe Ile Ile Pro Gln Cys Ser Leu Ala Pro Ser
            20                  25                  30

Ala Ile Ile Pro Gln Phe Leu Pro Pro Val Thr Ser Met Gly Phe Glu
        35                  40                  45

His Pro Ala Val Gln Ala Tyr Arg Leu Gln Leu Val Leu Ala Ala Ser
    50                  55                  60

Ala Leu Gln Gln Pro Ile Ala Gln Leu Gln Gln Gln Ser Leu Ala His
65                  70                  75                  80

Leu Thr Leu Gln Thr Ile Ala Thr Gln Gln Gln Gln Gln Phe Leu Pro
                85                  90                  95

Ser Leu Ser His Leu Ala Val Val Asn Pro Val Ala Tyr Leu Gln Gln
            100                 105                 110

Gln Leu Leu Ala Ser Asn Pro Leu Ala Leu Ala Asn Val Val Ala Asn
        115                 120                 125

Gln Gln Gln Gln Gln Leu Gln Gln Phe Leu Pro Ala Leu Ser Gln Leu
    130                 135                 140

Ala Met Val Asn Pro Ala Ala Tyr Leu Gln Gln Gln Gln Leu Leu Ser
145                 150                 155                 160

Ser Ser Pro Leu Ala Val Ala Asn Ala Pro Thr Tyr Leu Gln Gln Gln
                165                 170                 175

Leu Leu Gln Gln Ile Val Pro Ala Leu Thr Gln Leu Ala Val Ala Asn
            180                 185                 190

Pro Ala Ala Tyr Leu Gln Gln Leu Leu Pro Phe Asn Gln Leu Thr Val
        195                 200                 205

Ser Asn Ser Ala Ala Tyr Leu Gln Gln Arg Gln Gln Leu Leu Asn Pro
    210                 215                 220

Leu Ala Val Ala Asn Pro Leu Val Ala Ala Phe Leu Gln Gln Gln Gln
225                 230                 235                 240

Leu Leu Pro Tyr Asn Gln Phe Ser Leu Met Asn Pro Val Leu Ser Arg
                245                 250                 255

Gln Gln Pro Ile Val Gly Gly Ala Ile Phe
            260                 265

<210> SEQ ID NO 17
<211> LENGTH: 266
<212> TYPE: PRT
<213> ORGANISM: Zea mays
```

<400> SEQUENCE: 17

```
Met Ala Thr Lys Ile Leu Ala Leu Leu Ala Leu Leu Ala Leu Leu Val
1               5                   10                  15

Ser Ala Thr Asn Val Phe Ile Ile Pro Gln Cys Ser Leu Ala Pro Ser
            20                  25                  30

Ala Ile Ile Pro Gln Phe Leu Pro Pro Val Thr Ser Met Gly Phe Glu
        35                  40                  45

His Pro Ala Val Gln Ala Tyr Arg Leu Gln Leu Val Leu Ala Ala Ser
    50                  55                  60

Ala Leu Gln Gln Pro Ile Ala Gln Leu Gln Gln Ser Leu Ala His
65                  70                  75                  80

Leu Thr Leu Gln Thr Ile Ala Thr Gln Gln Gln Gln Gln Phe Leu Pro
                85                  90                  95

Ser Leu Ser His Leu Ala Val Val Asn Pro Val Ala Tyr Leu Gln Gln
            100                 105                 110

Gln Leu Leu Ala Ser Asn Pro Leu Ala Leu Ala Asn Val Val Ala Asn
        115                 120                 125

Gln Gln Gln Gln Leu Gln Gln Phe Leu Pro Ala Leu Ser Gln Leu
    130                 135                 140

Ala Met Val Asn Pro Thr Ala Tyr Leu Gln Gln Gln Leu Leu Ser
145                 150                 155                 160

Ser Ser Pro Leu Ala Val Ala Asn Ala Pro Thr Tyr Leu Gln Gln Gln
                165                 170                 175

Leu Leu Gln His Ile Val Pro Ala Leu Thr Gln Leu Ala Val Ala Asn
            180                 185                 190

Pro Ala Ala Tyr Leu Gln Gln Leu Pro Phe Asn Gln Leu Thr Val
        195                 200                 205

Ser Asn Ser Ala Ala Tyr Leu Gln Gln Arg Gln Gln Leu Leu Asn Pro
    210                 215                 220

Leu Ala Val Ala Asn Pro Leu Val Ala Ala Phe Leu Gln Gln Gln Gln
225                 230                 235                 240

Leu Leu Pro Tyr Asn Gln Phe Ser Leu Met Asn Pro Val Leu Ser Arg
                245                 250                 255

Gln Gln Pro Ile Val Gly Gly Ala Ile Phe
            260                 265
```

<210> SEQ ID NO 18
<211> LENGTH: 263
<212> TYPE: PRT
<213> ORGANISM: Zea mays

<400> SEQUENCE: 18

```
Met Ala Thr Lys Ile Leu Ala Leu Leu Ala Leu Leu Ala Leu Leu Val
1               5                   10                  15

Ser Ala Thr Asn Ala Phe Ile Ile Pro Gln Cys Ser Leu Ala Pro Ser
            20                  25                  30

Ala Ser Ile Pro Gln Phe Leu Pro Pro Val Thr Ser Met Gly Phe Glu
        35                  40                  45

His Pro Ala Val Gln Ala Tyr Arg Leu Gln Leu Ala Leu Ala Ala Ser
    50                  55                  60

Ala Leu Gln Gln Pro Ile Ala Gln Leu Gln Gln Ser Leu Ala His
65                  70                  75                  80

Leu Thr Leu Gln Thr Ile Ala Thr Gln Gln Gln Gln Gln Phe Leu
                85                  90                  95
```

Pro Ser Leu Ser His Leu Ala Val Val Asn Pro Val Thr Tyr Leu Gln
                100                 105                 110

Gln Gln Leu Leu Ala Ser Asn Pro Leu Ala Leu Ala Asn Val Ala Ala
            115                 120                 125

Tyr Gln Gln Gln Gln Leu Gln Gln Phe Met Pro Val Leu Ser Gln
130                 135                 140

Leu Ala Met Val Asn Pro Ala Val Tyr Leu Gln Leu Leu Ser Ser Ser
145                 150                 155                 160

Pro Leu Ala Val Gly Asn Ala Pro Thr Tyr Leu Gln Gln Leu Leu
                165                 170                 175

Gln Gln Ile Val Pro Ala Leu Thr Gln Leu Ala Val Ala Asn Pro Ala
            180                 185                 190

Ala Tyr Leu Gln Gln Leu Leu Pro Phe Asn Gln Leu Ala Val Ser Asn
                195                 200                 205

Ser Ala Ala Tyr Leu Gln Gln Arg Gln Gln Leu Leu Asn Pro Leu Ala
            210                 215                 220

Val Ala Asn Pro Leu Val Ala Thr Phe Leu Gln Gln Gln Gln Gln Leu
225                 230                 235                 240

Leu Pro Tyr Asn Gln Phe Ser Leu Met Asn Pro Ala Leu Gln Gln Pro
                245                 250                 255

Ile Val Gly Gly Ala Ile Phe
            260

<210> SEQ ID NO 19
<211> LENGTH: 46
<212> TYPE: DNA
<213> ORGANISM: Artificial Sequence
<220> FEATURE:
<223> OTHER INFORMATION: Primer Sequence A1-1

<400> SEQUENCE: 19
gaaggtgacc aagttcatgc tcccttttag tgagcgcaac aaatgt        46

<210> SEQ ID NO 20
<211> LENGTH: 45
<212> TYPE: DNA
<213> ORGANISM: Artificial Sequence
<220> FEATURE:
<223> OTHER INFORMATION: Primer sequence A2-1

<400> SEQUENCE: 20
gaaggtcgga gtcaacggat tccttttagt gagcgcaaca aatgc         45

<210> SEQ ID NO 21
<211> LENGTH: 25
<212> TYPE: DNA
<213> ORGANISM: Artificial Sequence
<220> FEATURE:
<223> OTHER INFORMATION: Primer sequence C1-1

<400> SEQUENCE: 21
ggagcaagtg agcactgtgg aataa                               25

<210> SEQ ID NO 22
<211> LENGTH: 40
<212> TYPE: DNA
<213> ORGANISM: Artificial Sequence
<220> FEATURE:
<223> OTHER INFORMATION: Primer Sequence A1-2

<400> SEQUENCE: 22
gaaggtgacc aagttcatgc tcacttgctc ctagtgccat       40

<210> SEQ ID NO 23
<211> LENGTH: 42
<212> TYPE: DNA
<213> ORGANISM: Artificial Sequence
<220> FEATURE:
<223> OTHER INFORMATION: Primer sequence A2-2

<400> SEQUENCE: 23
gaaggtcgga gtcaacggat tctcacttgc tcctagtgcc ag       42

<210> SEQ ID NO 24
<211> LENGTH: 25
<212> TYPE: DNA
<213> ORGANISM: Artificial Sequence
<220> FEATURE:
<223> OTHER INFORMATION: Primer sequence C1-2'

<400> SEQUENCE: 24
aactggtggg aggaactgtg aata       25

<210> SEQ ID NO 25
<211> LENGTH: 42
<212> TYPE: DNA
<213> ORGANISM: Artificial Sequence
<220> FEATURE:
<223> OTHER INFORMATION: Primer Sequence A1-3

<400> SEQUENCE: 25
gaaggtgacc aagttcatgc tcagctgctg ttgcaagtag gc       42

<210> SEQ ID NO 26
<211> LENGTH: 43
<212> TYPE: DNA
<213> ORGANISM: Artificial Sequence
<220> FEATURE:
<223> OTHER INFORMATION: Primer sequence A2-3

<400> SEQUENCE: 26
gaaggtcgga gtcaacggat tgcagctgct gttgcaagta ggt       43

<210> SEQ ID NO 27
<211> LENGTH: 22
<212> TYPE: DNA
<213> ORGANISM: Artificial Sequence
<220> FEATURE:
<223> OTHER INFORMATION: Primer sequence C1-3

<400> SEQUENCE: 27
tgagccacct agccgtggtg aa       22

<210> SEQ ID NO 28
<211> LENGTH: 42
<212> TYPE: DNA
<213> ORGANISM: Artificial Sequence
<220> FEATURE:
<223> OTHER INFORMATION: Primer Sequence A1-4

<400> SEQUENCE: 28
gaaggtgacc aagttcatgc tattgtacca gctctgactc at       42

<210> SEQ ID NO 29
<211> LENGTH: 42
<212> TYPE: DNA

<213> ORGANISM: Artificial Sequence
<220> FEATURE:
<223> OTHER INFORMATION: Primer sequence A2-4

<400> SEQUENCE: 29
gaaggtcgga gtcaacggat tattgtacca gctctgactc ag         42

<210> SEQ ID NO 30
<211> LENGTH: 20
<212> TYPE: DNA
<213> ORGANISM: Artificial Sequence
<220> FEATURE:
<223> OTHER INFORMATION: Primer sequence C1-4

<400> SEQUENCE: 30
caattggttg aatggaagca                                  20

<210> SEQ ID NO 31
<211> LENGTH: 47
<212> TYPE: DNA
<213> ORGANISM: Artificial Sequence
<220> FEATURE:
<223> OTHER INFORMATION: Primer Sequence A1-5

<400> SEQUENCE: 31
gaaggtgacc aagttcatgc taatggaagc aactgttgta agtaggt    47

<210> SEQ ID NO 32
<211> LENGTH: 46
<212> TYPE: DNA
<213> ORGANISM: Artificial Sequence
<220> FEATURE:
<223> OTHER INFORMATION: Primer sequence A2-5

<400> SEQUENCE: 32
gaaggtcgga gtcaacggat tatggaagca actgttgtaa gtaggc     46

<210> SEQ ID NO 33
<211> LENGTH: 26
<212> TYPE: DNA
<213> ORGANISM: Artificial Sequence
<220> FEATURE:
<223> OTHER INFORMATION: Primer sequence C1-5

<400> SEQUENCE: 33
cgtacctaca acaacagttg ctgcaa                           26

<210> SEQ ID NO 34
<211> LENGTH: 44
<212> TYPE: DNA
<213> ORGANISM: Artificial Sequence
<220> FEATURE:
<223> OTHER INFORMATION: Primer Sequence A1-6

<400> SEQUENCE: 34
gaaggtgacc aagttcatgc tggttgtatg gcagcaattg ttgc       44

<210> SEQ ID NO 35
<211> LENGTH: 46
<212> TYPE: DNA
<213> ORGANISM: Artificial Sequence
<220> FEATURE:
<223> OTHER INFORMATION: Primer sequence A2-6

<400> SEQUENCE: 35
gaaggtcgga gtcaacggat tctggttgta tggcagcaat tgttgt     46

```
<210> SEQ ID NO 36
<211> LENGTH: 23
<212> TYPE: DNA
<213> ORGANISM: Artificial Sequence
<220> FEATURE:
<223> OTHER INFORMATION: Primer sequence C1-6

<400> SEQUENCE: 36
cagtggctaa cccattggtc gct                                          23
```